US008846100B2

(12) United States Patent
Shojaei et al.

(10) Patent No.: US 8,846,100 B2
(45) Date of Patent: Sep. 30, 2014

(54) CONTROLLED DOSE DRUG DELIVERY SYSTEM

(75) Inventors: Amir Shojaei, Phoenixville, PA (US); Stephanie Read, Philadelphia, PA (US); Richard A. Couch, Bryn Mawr, PA (US); Paul Hodgkins, Exton, PA (US)

(73) Assignee: Shire LLC, Florence, KY (US)

( * ) Notice: Subject to any disclaimer, the term of this patent is extended or adjusted under 35 U.S.C. 154(b) by 1200 days.

(21) Appl. No.: 11/383,066

(22) Filed: May 12, 2006

(65) Prior Publication Data

US 2007/0264323 A1 Nov. 15, 2007

(51) Int. Cl.
*A61K 9/16* (2006.01)
*A61K 9/48* (2006.01)
*A61K 31/137* (2006.01)
*A61K 9/50* (2006.01)

(52) U.S. Cl.
CPC .............. *A61K 9/4808* (2013.01); *A61K 31/137* (2013.01); *A61K 9/5078* (2013.01); *A61K 9/1676* (2013.01)
USPC ............................ 424/490; 424/463; 424/493

(58) Field of Classification Search
USPC .................................. 424/489–502, 464–483
See application file for complete search history.

(56) References Cited

U.S. PATENT DOCUMENTS

| | | | |
|---|---|---|---|
| 2,099,402 | A | 11/1937 | Keller |
| 2,738,303 | A | 3/1956 | Blythe |
| 2,881,113 | A | 4/1959 | Millman |
| 3,048,526 | A | 8/1962 | Boswell |
| 3,066,075 | A | 11/1962 | Deutsch |
| 3,365,365 | A | 1/1968 | Butler et al. |
| 3,979,349 | A | 9/1976 | Fink et al. |
| 4,794,001 | A | 12/1988 | Mehta et al. |
| 5,137,733 | A | 8/1992 | Noda et al. |
| 5,202,159 | A | 4/1993 | Chen et al. |
| 5,328,697 | A | 7/1994 | Raman et al. |
| 5,411,745 | A | 5/1995 | Oshlack et al. |
| 5,422,121 | A | 6/1995 | Lehmann et al. |
| 5,496,561 | A | 3/1996 | Okada et al. |
| 5,501,861 | A | 3/1996 | Makino et al. |
| 5,618,559 | A | 4/1997 | Desai et al. |
| 5,733,575 | A | 3/1998 | Mehra et al. |
| 5,773,031 | A | 6/1998 | Shah et al. |
| 5,846,568 | A | 12/1998 | Olinger et al. |
| 6,005,027 | A | 12/1999 | Guillet et al. |
| 6,228,398 | B1 | 5/2001 | Devane et al. |
| 6,322,819 | B1 | 11/2001 | Burnside et al. |
| 6,475,493 | B1 | 11/2002 | Mulye |
| 6,605,300 | B1 * | 8/2003 | Burnside et al. .............. 424/452 |
| 6,749,867 | B2 | 6/2004 | Robinson et al. |
| 6,764,696 | B2 | 7/2004 | Pather et al. |
| 6,913,768 | B2 | 7/2005 | Couch et al. |
| RE41,148 | E | 2/2010 | Burnside et al. |
| 2003/0050620 | A1* | 3/2003 | Odidi et al. ................. 604/890.1 |
| 2003/0157173 | A1* | 8/2003 | Percel et al. .................. 424/473 |

FOREIGN PATENT DOCUMENTS

| | | |
|---|---|---|
| AU | 109438 | 1/1940 |
| EP | 0 640 337 | 3/1995 |
| JP | 59-082311 | 5/1984 |
| JP | 03-148215 | 6/1991 |
| JP | 07-061922 | 3/1995 |
| JP | 09-249557 | 9/1997 |
| JP | 09-267035 | 10/1997 |
| JP | 10-081634 | 3/1998 |
| WO | WO87/00441 | 1/1987 |
| WO | 97/03673 | 2/1997 |
| WO | 98/14168 | 4/1998 |
| WO | WO99/03471 | 1/1999 |
| WO | WO00/25752 | 5/2000 |
| WO | WO00/35450 | 6/2000 |
| WO | 2004028509 A1 | 4/2004 |

OTHER PUBLICATIONS

Adderall XR Package Inset, Sep. (2004).
Agyilirah GA and Banker SB, Polymers for Enteric Coating applications, Polymers for Controlled Drug Delivery (Peter J. Tarcha ed. 1991) 39-66.
American Chemical Society, Polymer Preprints, pp. 633-634, vol. 34, No. 1, Mar. 1993.
Ansel, et al., Rate Controlled Dosage Forms and Drug Delivery Systems, Pharmaceutical Dosage Forms and Drug Delivery Systems, 6th Ed. (1995), 213-222.
Answering Expert Report of Dr. Alexander M. Klibanov, expert for Shire Laboratories, Inc., Apr. 25, 2005.
Answering Expert Report of Robert Langer, Sc. D. Regarding United States Patent Nos. 6,322,819 and 6,605,300, expert for Shire Laboratories Inc., dated Apr. 25, 2005.
Barr Laboratories' Objections and Responses to Plaintiff Shire Laboratories Inc.'s Fifth Set of Interrogatories (No. 17), dated Sep. 3, 2004.
Barr Laboratories' Amended Answer, Affirmative Defenses and Counterclaims *Shire Laboratories, Inc. v. Barr Laboratories, Inc.*, Civil Action No. 03-CV-1219-PKC.
Barr Laboratories' Answer, Affirmative Defenses, and Counterclaims, dated Sep. 25, 2003.
Barr Laboratories Inc.'s Objections and Responses to Shire Laboratories Inc.'s Second Set of Interrogatories (Nos. 8-11), dated Feb. 18, 2004.
Barr Laboratories Inc.'s Objections and Responses to Shire Laboratories Inc.'s Fourth Set of Interrogatories (Nos. 15-16), dated Jul. 9, 2004.

(Continued)

*Primary Examiner* — Nissa Westerberg
*Assistant Examiner* — Micah-Paul Young
(74) *Attorney, Agent, or Firm* — McDermott Will & Emery LLP

(57) ABSTRACT

A multiple pulsed dose drug delivery system for pharmaceutically active amphetamine salts, comprising a pharmaceutically active amphetamine salt covered with an immediate-release coating and a pharmaceutically active amphetamine salt covered with an enteric coating wherein the immediate release coating and the enteric coating provide for multiple pulsed dose delivery of the pharmaceutically active amphetamine salt. The product can be composed of either one or a number of beads in a dosage form, including either capsule, tablet, or sachet method for administering the beads.

31 Claims, 10 Drawing Sheets

(56) References Cited

OTHER PUBLICATIONS

Barr Laboratories' Memorandum in Support of Its Motion to Amend Its Pleadings and exhibits thereto, dated Sep. 10, 2004.
Barr Laboratories' Memorandum in Support of Its Motion to Compel Production, dated Sep. 13, 2004.
Barr Laboratories' Supplemental Objections and Responses to Plaintiff Shire Laboratories Inc.'s Third Set of Interrogatories (Nos. 12-14)(Redacted), dated Aug. 27, 2004.
Barr Laboratories, Inc.'s '300 Notification Pursuant to §505(j)(2)(B)(ii) of the Federal Food, Drug and Cosmetic Act (21 U.S.C. §355(j)(2)(B)(ii) and 21 C.F.R. § 314.95).
Barr Laboratories, Inc.'s '819 Notification Pursuant to §505(j)(2)(B)(ii) of the Federal Food, Drug and Cosmetic Act (21 U.S.C. §355(j)(2)(B)(ii) and 21 C.F.R. § 314.95).
Bauer, et al., Cellulose Acetate Phthalate (CAP) and Trimellitate (CAT), Coated Pharmaceutical Dosage Forms (1998), 102-104.
Bodmeier et al., The Influence of Buffer Species and Strength on Diltiazem HCl Release from Beads Coated with the Aqueous Catinoc Polymer Dispersions, Eudragit RS, RL 30D, Pharmaceutical Research vol. 13, No. 1, 1996, 52-56.
Brown et al., Behavior and Motor Activity Response in Hyperactive Children and Plasma Amphetamine Levels Following a Sustained Release Preparation, Journal of the American Academy of Child Psychiatry, 19:225-239, 1980.
Brown et al., Plasma Levels of d-Amphetamine in Hyperactive Children, Psychopharmacology 62, 133-140, 1979.
Burns et al., A study of Enteric-coated Liquid-filled Hard Gelatin Capsules with Biphasic Release Characteristics, International Journal of Pharmaceutics 110 (1994) 291-296.
C. Lin et al., Bioavailability of d-pseudoephedrine and Azatadine from a Repeat Action Tablet Formulation, J Int Med Res (1982), 122-125.
C. Lin et al., Comparative Bioavailability of d-Pseudoephedrine from a Conventional d-Pseudoephedrine Sulfate Tablet and from a Repeat Action Tablet, J Int Med Res (1982) 10, 126-128.
Chan, Materials Used for Effective Sustained-Release Products, Proceedings of the International Symposium held on 29th to 31st of Jan. 1987 (The Bombay College of Pharmacy 1988), 69-84.
Chan, New Polymers for Controlled Products, Controlled Release Dosage Forms Proceedings of the International Symposium held on 29th to 31st of Jan. 1987 (The Bombay College of Pharmacy 1988) 59-67.
Chang et al., Preparation and Evaluation of Shellac Pseudolatex as an Aqueous Enteric Coating Systems for Pellets, International Journal of Pharmaceuticals, 60 (1990) 171-173.
Charles S. L. Chlao and Joseph R. Robinson, Sustained-Release Drug Delivery Systems, Remington: The Science and Pratice of Pharmacy, Tenth Edition (1995) 1660-1675.
Civil Docket for Case #: 1:03-cv-01164-GMS *Shire Laboratories, Inc. v. Impax Laboratories, Inc.*, Civil Action No. 03-CV-01164-GMS.
Civil Docket for Case #: 1:03-cv-01219-PKC-DFE *Shire Laboratories, Inc. v. Barr Laboratories, Inc.*, Civil Action No. 03-CV-1219-PKC.
Civil Docket for Case #: 1:03-cv-06632-VM-DFE *Shire Laboratories, Inc. v. Barr Laboratories, Inc.*, Civil Action No. 03-CV-6632-PKC.
Civil Docket for Case #: 1:05-cv-00020-GMS *Shire Laboratories, Inc. v. Impax Laboratories, Inc.*, Civil Action No. 05-20-GMS.
Cody et al., Amphetamine Enantiomer Excretion Profile Following Administration of Adderall, Journal of Analytical Toxicology, vol. 2, Oct. 2003, 485-492.
Complaint for Declaratory Judgment, *Impax Laboratories, Inc. v. Shire International Laboratories, Inc.* (Civ. Action No. 05772) and Exhibits attached thereto.
Daynes, Treatment of Noctural Enuresis with Enteric-Coated Amphetamine, The Practitioner, No. 1037, vol. 173, Nov. 1954.
Deposition of Transcript of Beth Burnside, dated Feb. 2, 2005.
Deposition of Transcript of Beth Burnside, dated Feb. 3, 2005.
Deposition of Transcript of Charlotte M. McGuiness, dated Aug. 6, 2004.
Deposition of Transcript of Donald John Treacy, Jr., dated Aug. 30, 2004.
Deposition of Transcript of Edward Rudnic, dated Jul. 28, 2004.
Deposition of Transcript of James J. Harrington, dated Jul. 27, 2005.
Deposition of Transcript of Kimberly Fiske, dated Sep. 17, 2004.
Deposition of Transcript of Richard Rong-Kun Chang, dated Jan. 20, 2005.
Deposition of Transcript of Richard A. Couch, dated Sep. 14, 2004.
Deposition of Transcript of Robert Schaffer, dated Aug. 17, 2005.
Deposition of Transcript of Xiaodi Guo, dated Jan. 24, 2005.
Deposition of Transcript of Xiaodi Guo, dated Jul. 26, 2004.
Deposition transcript of Honorable Gerald J. Mossinghoff and exhibits thereto, dated Jun. 8, 2005.
Deposition Transcript of Richard Chang, dated Sep. 8, 2004.
Edward Stempel, Prolonged Drug Action, HUSA's Pharmaceutical Dispensing, Sixth Edition, 1996, 464, 481-485.
Expert Report of Dr. Joseph R. Robinson, expert for Barr Laboratories and exhibits thereto, Feb. 28, 2005.
Expert Report of the Honorable Gerald J. Mossinghoff, expert for Barr Laboratories, Inc. and exhibits thereto, Mar. 16, 2005.
Freedom of Information Request Results for—Dexadrine (SmithKline Beecham): May 20, 1976 Disclosable Approval Information.
Fukumori, Coating of Multiparticulates Using Polymeric Dispersions, Multiparticulate Oral Drug Delivery (Swarbrick and Selassie eds. 1994),79-110.
Garnett et al., Pharmacokinetic Evaluation of Twice-Daily Extended-Release Carbamazepine(CBZ) and Four-Times-Daily Immediate-Release CBZ in Patients with Epilepsy, Epilepsia 39(3): 274-279, 1998.
Glatt, The World of the Fluid Bed, Fluid Bed Systems, 1-19.
Goodhart et al., An evaluation of Aqueous Film-forming Dispersions for Controlled Release, Pharmaceutical Technology, Apr. 1984, 64-71.
Greenhill et al., A Pharmacokinetic/Pharmacodynamic Study Comparing a Single Morning Dose of Adderall to Twice-Daily Dosing in Children with ADHD. J. Am. Acad. Adolesc. Psychiatry, 42:10, Oct. 2003.
Guidance for Industry: Extended Release Oral Dosage Forms: Development, Evaluation, and Application of In Vitro/In Vivo Correlations (1997).
Guidance for Industry: Food-Effect Bioavailability and Fed Bioequivalence Studies (2002).
Guidance for Industry: SUPAC-MR: Modified Release Solid Oral Dosage Forms (1997).
Hall HS and Pondell RE, Controlled Release Technologies: Methods, Theory, and Applications, pp. 133-154 (Agis F. Kydonieus ed. 1980).
Handbook of Pharmaceutical Excipients: Ethycellulose, Polymethacrylates, 4th ed. (2003), 237-240, 462-468.
Handbook of Pharmaceutical Excipients: Polymethacrylates, 2nd Ed. (1994), 361-366.
Hans-Martin Klein & Rolf W. Gunther, Double Contrast Small Bowl Follow-Through with an Acid-Resistant Effervescent Agent, Investigative Radiology vol. 28, No. 7, Jul. 1993, 581-585.
Harris, et al., Aqueous Polymeric Coating for Modified-Release Pellets, Aqueous Polymeric Coating for Pharmaceutical Dosage Forms (McGinity ed., 1989), 63-79.
Hawley's Condensed Chemical Dictionary 13th Ed. 1997, 584, 981.
Holt, Bioequivalence Studies of Ketoprofen: Product formulation, Pharmacokinetics, Deconvolution, and In Vitro-In Vivo correlations, Thesis submitted to Oregon State University, Aug. 20, 1997 (1997).
Husson et al., Influence of Size Polydispersity on Drug Release from Coated Pellets, International Journal of Pharmaceutics, 86 (1992) 113-121, 1992.
Impax Laboratories Answer and Affirmative Defenses *Shire Laboratories, Inc. v. Impax Laboratories, Inc.*, Civil Action No. 03-CV-01164-GMS.
Impax Laboratories, Inc.'s First Supplemental Responses to Shire Laboratories Inc.'s First Set of Interrogatories (Nos. 11-12) dated Mar. 28, 2005.

(56) References Cited

OTHER PUBLICATIONS

Impax Laboratories, Inc.'s Memorandum in Support of the Motion to Amend Its Answer dated Feb. 25, 2005 and exhibits thereto.

Impax Laboratories, Inc.'s Reply Memorandum in Support of the Motion to Amend Its Answer dated Mar. 18, 2005 and exhibits thereto.

Impax Laboratories, Inc's First Amended Answer and Affirmative Defenses, dated May 2, 2005.

Ishibashi et al., Design and Evaluation of a New Capsule-type Dosage Form for Colon-targeted Delivery of Drugs, International Journal of Pharmaceutics 168, (1998) 31-40.

J. Sjogren, Controlled Release Oral Formulation technology, Rate Control in Drug Therapy, (1985) 38-47.

Jarowski, The Pharmaceutical Pilot Plant, Pharmaceutical Dosage Forms: Tablets, vol. 3, 2nd Ed. (1990), 303-367.

Kao et al., Lag Time Method to Delay Drug release to Various Sites in the Gastrointestinal Tract, Journal of Controlled Release 44(1997) 263-270.

Kiriyama et al., The Bioavailability of Oral Dosage Forms of a New HIV-1 Protease Inhibitor, KNI-272, in Beagle Dogs, Biopharmaceutics & Drug Disposition, vol. 17 125-234 (1996).

Klaus Lehmann, Coating of Multiparticulates Using Polymeric Solutions, Multiparticulate Oral Drug Delivery (Swarbrick and Sellassie ed., 1994) 51-78.

Krowczynski & Brozyna, Extended-Release Dosage Forms pp. 123-131 (1987).

Leon Lachman, Herbert A. Liebeman, Joseph L. Kanig, The Theory and Practice of Industrial Pharmacy, Second Edition (1976) 371-373.

Leopold & Eikeler, Eudragit E as Coating Material for the pH-Controlled Drug Release in the Topical Treatment of Inflammatory Bowel Disease (IBD), Journal of Drug Targeting, 1998, vol. 6, No. 2, pp. 85-94.

Lin & Cheng, In-vitro Dissolution Behaviour of Spansule-type Micropellets Prepared by Pan Coating Method, Pharm. Ind. 51 No. 5 (1989) 528-531.

Liu et al., Comparative Release of Phenylprepanolamine HCl from Long-Acting Appetite Suppressant Product: Acutrim vs. Dexatrim, Drug Development and Industrial Pharmacy, 10(10), 1639-1661 (1984).

Marcotte, et al., Kinetics of Protein Diffusion from a Poly(D, L-Lactide) Reservoir System. Journal of Pharmaceutical Sciences vol. 79, No. 5, May 1990.

Mathir, et al., In vitro characterization of a controlled-release chlorpheniramine maleate delivery system prepared by the air-suspension technique, J. microencapsulation, vol. 14, No. 6, 743-751 (1997).

McGough, et al., Pharmacokinetics of SL1381 (Adderall XR), an Extended-Release Formulation of Adderall, Journal of the American Academy of Child & Adolescent Psychiatry, vol. 42, No. 6, Jun. 2003, 684-691.

McGraw-Hill Dictionary of Scientific and Technical Terms, 5th Ed. (1994), 97,972.

Mehta, et al., Evaluation of Fluid-bed Processes for Enteric Coating Systems, Pharmaceutical Technology, Apr. 1986, 46-56.

Moller, Dissolution Testing of delayed Release Preparations, Proceedings of the International Symposium held on 29th to 31st of Jan. 1987 (the Bombay College of Pharmacy 1988), 85-111.

Response to Office Action filed May 2, 2006 in U.S. Appl. No. 11/091,010.

Office Action in U.S. Appl. No. 11/091,010, mailed Feb. 3, 2006.

Office Action in U.S. Appl. No. 11/091,010, mailed Jul. 13, 2006.

Response to Office Action filed Jul. 18, 2006 in U.S. Appl. No. 11/091,010.

Office Action in U.S. Appl. No. 11/091,010, mailed Oct. 10, 2006.

Office Action mailed Mar. 2, 2005 in European Patent Application No. 99 970594.0-2123.

Opening Expert Report of Dr. Michael Mayersohn, expert for Impax Laboratories Inc. and exhibits thereto, Mar. 12, 2005.

Opening Expert Report of Dr. Walter Chambliss, expert for Impax Laboratories, Inc. and exhibits thereto, Mar. 15, 2005.

Order Construing the Terms of U.S. Patent Nos. 6,322,819 and 6,605,300 *Shire Laboratories, Inc.* v. *Impax Laboratories, Inc.*, Civil Action No. 03-CV-01164-GMS.

PDR Drug information for Ritalin LA Capsules, Apr. (2004).

Pelham, et al., A Comparision of Morning-Only and Morning/Late Afternoon Adderall to Morning-Only, Twice-daily, and Three Times-Daily Methyphenidate in Children with Attention-Deficit/Hyperactivity Disorder, Pediatrics, vol. 104, No. 6, Dec. 1999.

Physicians' Desk Reference: Adderall, 51st Ed. (1997).

Physicians' Desk Reference: Adderall, 56th Ed. (2002).

Physicians' Desk Reference: Dexedrine, 56th ed. (2002).

Physicians' Desk Reference: Ritalin, 56th Ed. (2002).

Porter and Bruno, Coating of Pharmaceutical Solid-Dosage Forms, 77-160.

Prescribing Information: Dexedrine, brand of dextroamphetamine sulfate (2001).

R. Bianchini & C. Vecchio, Oral Controlled Release Optimization of Pellets Prepared by Extrusion-Spheronization Processing, IL Farmaco 44(6), 645-654, 1989.

Rambali, et al., Using experimental design to optimize the process parameters in fluidized bed granulation on a semi-full scale, International Journal of Pharmaceutics 220 (2001) 149-160.

Remington: The Science and Practice of Pharmacy, Basic Pharmacokinetics, 16th Ed. (1980), 693.

Remington: The Science and Practice of Pharmacy, Elutriation, 20th Ed.(2000), 690.

Remington's Pharmaceutical Sciences, Fifteenth Edition (1975) 1624-1625.

Remington's Pharmaceutical Sciences, RPS XIV, 1700-1714.

Reply to Barr Laboratories Inc.'s Amended Answer, Affirmatice Defenses and Counterclaims *Shire Laboratories, Inc.* v. *Barr Laboratories, Inc.*, Civil Action No. 03-CV-1219-PKC.

Reply to Barr Laboratories Inc.'s Amended Answer, Affirmatice Defenses and Counterclaims *Shire Laboratories, Inc.* v. *Barr Laboratories, Inc.*, Civil Action No. 03-CV-6632-PKC.

Rong-Kun Chang and Joseph R. Robinson, Sustained Drug Release from Tablets and Particles Through Coating, Pharmaceutical Dosage Forms: Tablets (Marcel Dekker, Inc. 1990), 199-302.

Rong-Kun Chang et al., Formulation Approaches for Oral Pulsatile Drug Delivery, American Pharmaceutical Review.

Rong-Kun Chang, A Comparision of Rheological and Enteric Properties among Organic Solutions, Ammonium Salt Aqueous Solutions, and Latex Systems of Some Enteric Polymers, Pharmaceutical Technology, Oct. 1990, vol. 14, No. 10, 62-70.

Rosen, et al., Absorption and Excretion of Radioactively Tagged Dextroamphetamine Sulfate from a Sustained-Release Preparation, Journal of the American Medical Association, Dec. 13, 1965, vol. 194, No. 11, 1203-1205.

Scheiffele, et al., Studies Comparing Kollicoat MAE 30 D with Commercial Cellulose Derivatives for Enteric Coating on Caffeine Cores, Drug Development and Industrial Pharmacy, 24(9), 807-818 (1998), 807-818.

Serajuddin, et al., Selection of Solid Dosage Form Composition through Drug-Excipient Compatibility Testing, Journal of Pharmaceutical Sciences vol. 88, No. 7, Jul. 1999, 696-704.

Shargel; Pharmacokinetics of Oral Absorption, Applied Biopharmaceutics & Pharmacokinetics. 5th Ed. (225), 164-166.

Sheen et al., Aqueous Film Coating Studies of Sustained Release Nicotinic Acid Pellets: An In-Vitro Evaluation, Drug Development and Industrial Pharmacy, 18(8), 851-860 (1992).

Shire Laboratories Inc.'s Opposition to Barr Laboratories' Motion to Amend Its Answers and Counterclaims, Sep. 15, 2004.

Slattum, et al., Compararision of Methods for the Assessment of Central Nervous System Stimulant Response after Dextroamphetamine Administration to Healthy Male Volunteers, J. clin Pharmacol (1996) 36,1039-1050.

Sprowls' American Pharmacy: An Introduction to Pharmaceutical Techniques and Dosage Forms, 7th Ed. (1974), 387-388.

Sriamornsak, et al., Development of Sustained Release Theophylline Pellets Coated with Calcium Pectinate, Journal of Controlled Release 47 (1997) 221-232.

(56) References Cited

OTHER PUBLICATIONS

Stevens, et al., Controlled, Multidose, Pharmacokinetic Evaluation of Two Extended-Release Carbamazepine Formulations (carbatrol and Tegretol-XR), Journal of Pharmaceutical Sciences vol. 87, No. 12, Dec. 1998, 1531-1534.
Teva Notice letter dated Feb. 21, 2005.
Teva Notice letter dated Jun. 1, 2005.
The Merck Index: Amphetamine, 12th Ed., 620.
The Merck Index: Amphetamine, 13th Ed. (2001), 97, 1089.
The United States Pharmacopeia 23, National Formulary 18 (1995) pp. 1791-1799.
The United States Pharmacopeia 26, National Formulary 21 (2003) pp. 2157-2165.
The United States Pharmacopeia 27, National Formulary 22 (2004) pp. 2302-2312.
Treatise on Controlled Drug Delivery, pp. 185-199 (Agis Kydonieus ed. 1992).
Tulloch, et al., SL 1381 (Adderall XR), a Two-component, Extended-Release Formulation of Mixed Amphetamine Salts: Bioavailability of Three Test formulations and Comparision of Fasted, Fed, and Sprinkled Administration, Pharmacotherapy vol. 22, No. 11, (2002), 1405-1415.
Vasilevska, et al., Preparation and Dissolution Characteristics of Controlled Release Diltiazem Pellets, Drug Development and Industrial Pharmacy, 18(15), 1649-1661 (1992).
Watano, et al., Evaluation of aqueous Enteric Coated Granules Prepared by Moisture Control Method in Tumbling Fluidized Bed Process, Chem. Pharm. Bull. 42(3) 663-667 (1994).
Wesdyk, et al., Factors affecting differences in film thickness of beads coated in fluidized bed units, International Journal of Pharmaceutics, 93, 101-109, (1993).
Wouessidjewe, Aqueous polymethacrylate Dispersions as Coating Materials for Sustained and Enteric Release Systems, S.T.P. Pharma Sciences 7(6) 469-475 (1997).
Barr Laboratories' Amended Answer, Affirmative Defenses and Counterclaims *Shire Laboratories, Inc. v. Barr Laboratories, Inc.*, Civil Action No. 03-CV-6632-PKC, dated Sep. 27, 2004.
Court Docket for *Shire Laboratories Inc. v. Teva Pharmaceutical Industries Ltd.*, Case No. 2:06-cv-00952-SD dated Jan. 8, 2007.
Complaint in *Shire Laboratories Inc. v. Teva Pharmaceutical Industries Ltd.*, and exhibits thereto, Case No. 2:06-cv-00952-SD dated Mar. 2, 2006.
Answer and Counterclaims in *Shire Laboratories Inc. v. Teva Pharmaceutical Industries Ltd.*, Case No. 2:06-cv-00952-SD dated Jul. 24, 2006.
Reply to Counterclaims in *Shire Laboratories Inc. v. Teva Pharmaceutical Industries Ltd.*, Case No. 2:06-cv-00952-SD dated Aug. 16, 2006.
Defendants' Responses to Plaintiff Shire's First Set of Interrogatories (1-12) in *Shire Laboratories Inc. v. Teva Pharmaceutical Industries Ltd.*, Case No. 2:06-cv-00952-SD dated Sep. 20, 2006.
Defendants' Responses to Plaintiffs First Set of Request for the Production of Documents and Things (1-70) in *Shire Laboratories Inc. v. Teva Pharmaceutical Industries Ltd.*, Case No. 2:06-cv-00952-SD dated Oct. 4, 2006.
Plaintiff's Response to Defendants' First Set of Interrogatories in *Shire Laboratories Inc. v. Teva Pharmaceutical Industries Ltd.*, Case No. 2:06-cv-00952-SD dated Oct. 11, 2006.
Plaintiffs Response to Defendants' First Set of Production Requests in *Shire Laboratories Inc. v. Teva Pharmaceutical Industries Ltd.*, Case No. 2:06-cv-00952-SD dated Oct. 11, 2006.
Defendants' Responses to Plaintiffs Second Set of Requests for the Production of Documents and Things (71-80) in *Shire Laboratories Inc. v. Teva Pharmaceutical Industries Ltd.*, Case No. 2:06-cv-00952-SD dated Nov. 8, 2006.
Defendants' Responses to Plaintiff Shire's Second Set of Interrogatories (No. 13) in *Shire Laboratories v. Teva Pharmaceuticals Industries Ltd.*, Case No. 2:06-cv-00952-SD dated Nov. 8, 2006.
Petition Under Section 8 and exhibits thereto, submitted to the Canadian Patent Office on Dec. 4, 2006.
Office Action in U.S. Appl. No. 11/091,011, mailed Dec. 1, 2006.
Response to Non-Final Office Action filed Jan. 10, 2007 in U.S. Appl. No. 11/091,011.
Response to Non-Final Office Action filed Jan. 10, 2007 in U.S. Appl. No. 11/091,010.
Neville et al., *Disintegration of Dextran Sulfate Tablet Products: Effect of Physicochemical Properties*, Drug Development and Industrial Pharmacy, New York, NY, vol. 18, No. 19, Jan. 1, 1992, pp. 2067-2079, XP009092848, ISSN: 0363-9045.
Patrick et al., *Pharmacology of Methylphenidate, Amphetamine Enantiomers and pemoline in Attention-Deficit Hyperactivity Disorder*, Human Psychopharmacology, vol. 12, pp. 527-546 (1997).
Chaumeil et al., *Enrobages gastro-resistants a l'acetophtalate de cellulose*, Annales Pharmaceutiques Francaises, 1973, No. 5, pp. 375-384.
Wigal, et al., Evaluation of Individual Subjects in the Analog Classroom Setting; II. Effects of Dose of Amphetamine (Adderall), Psychopharmacology Bulletin, vol. 34, No. 4, pp. 833-838, 1998.
Communication pursuant to Article 96(2) EPC dated Jun. 21, 2006 for corresponding E application No. EP99 970 594.0.
International Search Report dated Nov. 21, 2006 issued for corresponding International Application No. PCT/US06/18453.
U.S. Appl. No. 11/091,011: Final Office Action dated Nov. 13, 2009, including Form PTO-892 and the references cited therein (10 pages).
Office Action in Japanese Application No. 2008-159637 dated Sep. 11, 2012 (Original Japanese and English Translation attached).
Conte et al., "Press-coated tablets for time-programmed release of drugs," *Biomaterials*, vol. 14, No. 13, pp. 1017-1023 (1993).
Gazzaniga et al., "Oral Chronotopic Drug Delivery Systems: Achievement of Time and/or Site Specificity," *Eur J Pharm Biopharm*, vol. 40, No. 4, pp. 246-250 (1994).
Theeuwes, "Oros Osmotic System Development," *Drug Dev Ind Pharm*, vol. 9, No. 7, pp. 1331-1357 (1983).
Walia et al., "Preliminary Evaluation of an Aqueous Wax Emulsion for Controlled-Release Coating," Pharm Dev Tech, vol. 3, No. 1, pp. 103-113 (1998).
Xu et al., "Programmable Drug Delivery from an Erodible Association Polymer System," Pharm Res, vol. 10, No. 8, pp. 1144-1152 (1993).
Office Action dated Feb. 18, 2014, which is issued during the prosecution of Mexican Patent Application No. MX/a/2008/014455, which is related to the present application together with a letter from a foreign agent re. the Office Action in English.

* cited by examiner

SPD465 Sustained Release Capsule

Dissolution Profile of SPD465 12.5mg Capsules Lot# A03552A

Dissolution Profile of SPD465 25mg Capsules Lot# A03547A

Dissolution Profile of SPD465 37.5mg Capsules Lot# A03549B

Dissolution Profile of SPD465 50mg Capsules Lot# A03536B

CONTROLLED DOSE DRUG DELIVERY SYSTEM

BACKGROUND OF THE INVENTION

Traditionally, drug delivery systems have focused on constant/sustained drug output with the objective of minimizing peaks and valleys of drug concentrations in the body to optimize drug efficacy and reduce adverse effects. Reduced dosing frequency and improved patient compliance can also be expected for constant/sustained release drug delivery systems, compared to immediate release preparations. However, for certain drugs, sustained release delivery is not suitable and is affected by the following factors:

First pass metabolism: Some drugs, such as β-blockers, β-estradiol, and salicylamide, undergo extensive first pass metabolism and require fast drug input to saturate metabolizing enzymes in order to minimize pre-systemic metabolism. Thus, a constant/sustained oral method of delivery would result in reduced oral bioavailability.

Biological tolerance: Continuous release drug plasma profiles are often accompanied by a decline in the pharmacotherapeutic effect of the drug, e.g., biological tolerance of transdermal nitroglycerin.

Chronopharmacology and circadian rhythms: Circadian rhythms in certain physiological functions are well established. It has been recognized that a symptom or disease onset can occur during specific time periods of the 24 hour day, e.g., asthma and angina pectoris attacks are most frequently in the morning hours (Lemmer, B, J Controlled Release. 1991; 16:63-74; Lemmer B, Pulsatile Drug Delivery: Current Applications and Future Trends (R Gurney, H E Junginger, N A Peppas, eds.) 1993; 11-24).

Local therapeutic need: For the treatment of local disorders such as inflammatory bowel disease, the delivery of compounds to the site of inflammation with no loss due to absorption in the small intestine is highly desirable to achieve the therapeutic effect and to minimize side effects.

Gastric irritation or drug instability in gastric fluid: For compounds with gastric irritation or chemical instability in gastric fluid, the use of a sustained release preparation may exacerbate gastric irritation and chemical instability in gastric fluid.

Drug absorption differences in various gastrointestinal segments: In general, drug absorption is moderately slow in the stomach, rapid in the small intestine, and sharply declining in the large intestine. Compensation for changing absorption characteristics in the gastrointestinal tract may be important for some drugs. For example, it is rational for a delivery system to pump out the drug much faster when the system reaches the distal segment of the intestine, to avoid the entombment of the drug in the feces.

Pulsed dose delivery systems, prepared as either single unit or multiple unit formulations, and which are capable of releasing the drug after a predetermined time, have been studied to address the aforementioned problematic areas for sustained release preparations. These same factors are also problematic in pulsed dose formulation development. For example, gastrointestinal transit times vary not only from patient to patient but also within patients as a result of food intake, stress, and illness; thus a single-unit pulsed-release system may exhibit higher variability compared to a multiple unit system. Additionally, drug layering or core making for multiple unit systems is a time-consuming and hard-to-optimize process. Particularly challenging for formulation scientists has been overcoming two conflicting hurdles for pulsatile formulation development, i.e., lag time and rapid release.

Various enteric materials, e.g., cellulose acetate phthalate, hydroxypropyl methylcellulose phthalate, polyvinyl acetate phthalate, and the EUDRAGIT® acrylic polymers, have been used as gastroresistant, enterosoluble coatings for single drug pulse release in the intestine (Xu X and Lee P, Pharm Res. 1993; 10(8):1144-1152). The enteric materials, which are soluble at higher pH values, are frequently used for colon-specific delivery systems. Due to their pH-dependent attributes and the uncertainty of gastric retention time, in-vivo performance as well as inter- and intra-subject variability are major issues for using enteric coated systems as a time-controlled release of drugs.

A retarding, swellable hydrophilic coating has been used for oral delayed release systems (Gazzaniga et al., Eur J Pharm Biopharm. 1994; 40(4):246-250; Gazzaniga et al., S.T.P. Pharma Sciences. 1996; 5(1):83-88). It was demonstrated that lag time was linearly correlated with coating weight gain and drug release was pH independent.

Hydroxypropyl methylcellulose barriers with erodible and/or gellable characteristics formed using press coating technology for tablet dosage forms have been described to achieve time-programmed release of drugs (Conte et al., Biomaterials. 1993; 14(13):1017-1023). Barrier formulation variables (such as grade of hydroxypropyl methylcellulose, water-soluble and water-insoluble excipients) significantly altered the lag time and the release rate from the center cores.

Special grades of hydroxypropyl methylcellulose, e.g., METOLOSE® 60SH, 90SH (Shin-Etsu Ltd., Japan), and METHOCEL® F4M (Dow Chemical Company, USA) have been used as a hydrophilic matrix material to achieve bimodal drug release for several drugs, i.e., aspirin, ibuprofen, and adinazolam (WO 87/00044). Bimodal release is characterized by a rapid initial release, followed by a period of constant release, and then by a second rapid drug release.

Tablets or capsules coated with a hydrophobic wax-surfactant layer, made from an aqueous dispersion of carnauba wax, beeswax, polyoxyethylene sorbitan monooleate, and hydroxypropyl methylcellulose have been used for rapid drug release after a predetermined lag time. However, even though a two-hour lag time was achieved for the model drug theophylline at a higher coating level (60%), three hours were required for a complete release of theophylline after the lag time. (Walia et al., Pharm Dev Tech. 1998; 3(1):103-113)

A sustained-release drug delivery system is described in U.S. Pat. No. 4,871,549. When this system is placed into dissolution medium or the gastrointestinal tract, water influx and the volume expansion of the swelling agent cause the explosion of the water permeable membrane. The drug thus releases after a predetermined time period.

The OROS® push-pull system (Alza Company) has been developed for pulsatile delivery of water-soluble and water-insoluble drugs (Theeuwes, Drug Dev Ind Pharm. 1983; 9(7): 1331-1357; Theeuwes F, Novel Drug Delivery and Its Therapeutic Application (L F Prescott and W S Nimmos eds.) 1989; 323-340), e.g. the OROS-CT® system and is based on the swelling properties of an osmotic core compartment which provides a pH-independent, time-controlled drug release.

The PULSINCAP® dosage form releases its drug content at either a predetermined time or at a specific site (e.g., colon) in the gastrointestinal tract (WO 90/09168). The drug formulation is contained within a water-insoluble capsule body and is sealed with a hydrogel plug. Upon oral administration, the capsule cap dissolves in the gastric juice and the hydrogel plug swells. At a controlled and predetermined time point, the swollen plug is ejected from the PULSINCAP® dosage form and the encapsulated drug is released. A pulsatile capsule system containing captopril with release after a nominal 5-hr period was found to perform, reproducible in dissolution and gamma scintigraphy studies. However, in the majority of subjects, no measurable amounts of the drug were observed in the blood, possibly due to instability of the drug in the distal intestine. (Wilding et al., Pharm Res. 1992; 9(5):654-657)

ADDERALL® is an immediate release composition, which includes a mixture of four amphetamine salts: dextroamphetamine sulfate, dextroamphetamine saccharate, amphetamine aspartate monohydrate and amphetamine sulfate. This combination of amphetamines is indicated for the treatment of Attention Deficit Hyperactivity Disorder in children from 3-10 years of age.

One disadvantage of immediate release-only treatments for children is that two separate doses are administered, one in the morning and one approximately 4-6 hours later, commonly away from home under other than parental supervision. This requires a second treatment, which is time-consuming, inconvenient and may be problematic for those children having difficulties in swallowing tablet formulations. ADDERALL XR® met the need for a dosage form, which can be administered once, in place of the two oral doses which are needed using the conventional drug delivery formulations of the prior art. See U.S. Pat. Nos. 6,322,819 and 6,605,300; co-pending Reissue application Ser. Nos. 11/091, 010 and 11/091,011.

There are currently two medications (ADDERALL XR® and STRATTERA™) approved by the U.S. Food and Drug Administration (FDA) for the treatment of ADHD in adults. ADDERALL XR® is a mixed amphetamine salts medication. STRATTERA™ is an atomoxetine (a norepinephrine reuptake inhibitor) medication. Long acting stimulant preparations, such as ADDERALL XR® and CONCERTA® (methylphenidate), are designed to provide a duration of effect up to 12 hours. However, clinicians have noted that a proportion of patients treated with these formulations require additional treatment with a short-acting stimulant to extend the daily therapeutic effect. For patients taking long-acting stimulant formulations who require duration of clinical benefit beyond 10-12 hours, clinicians have augmented the morning long-acting formulation, typically at 8-10 hours post-dose, with a dose of the same immediate-release (IR) medication. Typically, the dose of the IR medication is smaller than the long-acting dose. This augmentation strategy is most relevant to the "longer day demands" of adult and adolescents, rather than school age, pediatric patients.

Thus, a need exists for a once-daily, long-acting oral composition that provides effective treatment of ADHD, without supplementation, for patients with longer day demands (e.g., 14-16 awake hours).

SUMMARY OF THE INVENTION

The present invention provides a long-acting amphetamine pharmaceutical composition, which includes an immediate release component, a delayed pulsed release component and a sustained release component, to meet the therapeutic needs for ADHD patients with longer-day demands. The present invention fills the need for once-daily longer-day treatment of ADHD by providing an amphetamine pharmaceutical composition that is bioequivalent to an equal dosage of ADDERALL XR® followed by an IR amphetamine composition 8 hours later.

The addition of a second delayed pulsed release formulation, having a lag time of about 8 hours, to ADDERALL XR® cannot, as one might expect, meet the recognized need for a once-daily long-acting amphetamine composition that meets a patient's longer day requirements (i.e., a once-daily amphetamine composition that is bioequivalent to ADDERALL XR® plus an immediate release amphetamine composition administered 8 hours later). A delayed pulsed formulation having a lag time of about 8 hours would be unsuitable because it would release the active agent in the distal gastrointestinal tract (the colon), resulting in decreased absorption of the active agent.

Unexpectedly, it has been discovered that a sustained release formulation administered in combination with immediate release and delayed pulsed release components similar to those present in ADDERALL XR® can mimic the bioavailability of an equivalent total amphetamine dosage provided by ADDERALL XR® followed by an immediate release amphetamine composition 8 hours later. However, the "usual" or "typical" construction for a sustained release formulation is not suitable. Typically, a sustained release formulation is constructed with a delayed release coating overlaying a sustained release coating. Such a usual or typical sustained release construction results in a Tmax that is too early after administration to a patient to result in a composition that meets the longer-day requirements for the treatment of ADHD. For example, the dissolution profiles for a typical sustained release formulation (PD0149-124) and a sustained release formulation of the present invention (PD0149-120) are illustrated in FIG. 1. PD0149-124 has a typical sustained release formulation construction, wherein the immediate release bead of Example 1 (see Examples 1 and 2, infra) is coated with a sustained release coating (SURELEASE®), the sustained release coating is coated with a delayed release coating (EUDRAGIT® FS30 D), and the delayed release coating is coated with a protective layer (OPADRY®). PD0149-120 is an embodiment of a sustained release formulation of the present invention. PD0149-120 has a construction wherein the immediate release bead of Example 1 is coated with a delayed release coating (EUDRAGIT® FS30 D), the delayed release coating is coated with a protective coating (OPADRY®), and the protective coating is coated with a sustained release coating (SURELEASE®). As illustrated in FIG. 1, PD0149-120 provides a later Tmax relative to a typically-constructed sustained release formulation, PD0149-124.

According to the present invention, an atypical, counter-intuitive construction for a sustained release amphetamine formulation, when administered in combination with an immediate release formulation and a delayed pulsed release formulation, is bioequivalent to ADDERALL XR® followed by an immediate release amphetamine formulation administered 8 hours later. A sustained release formulation of the present invention comprises at least one amphetamine salt layered onto, or incorporated into, a core; a delayed release coating layered onto the amphetamine core; a sustained release coating layered onto the delayed release coating; and, optionally, a protective coating. See FIG. 2. In a preferred embodiment, the delayed release component is pH dependent.

A sustained release pharmaceutical formulation of the present invention can comprise about 10% to about 150% of the amphetamine dosage of the immediate release mixed amphetamine salt composition and/or an extended release mixed amphetamine salt composition. For example, the sustained release formulation can be administered, in the same or different dosage forms, with the IR and delayed pulsed release components of ADDERALL XR® in an amphetamine dosage ratio of 1:1:1 (e.g., 10 mg immediate release amphetamine, 10 mg delayed pulsed release amphetamine, 10 mg sustained release amphetamine). Thus, in this example, the sustained release composition comprises about 33% of the total amphetamine dose. In another example, a patient with ADHD and insomnia can be administered a reduced amount of the sustained release composition, e.g., 10 mg immediate release amphetamine, 10 mg delayed pulsed release amphetamine, and 5 mg sustained release amphetamine (the sustained release composition comprises 20% of the total amphetamine dose). Thus, according to the present invention, a clinician can adjust the sustained release formulation dosage to meet the needs of an individual patient suffering from ADHD.

The pharmaceutical composition of the present invention, comprising an immediate release amphetamine component, a delayed pulsed release amphetamine component and a sustained release amphetamine component, delivers, in a single dose, mixed amphetamine salts to a patient with a pharmacokinetic profile similar to a 2-dose treatment with a currently available commercial extended release composition (i.e., ADDERALL XR®) plus an immediate release composition administered about eight hours after the ADDERALL XR®. See, for example, FIG. 9. This similarity in bioequivalence is surprising because it would be expected that some part of the drug delivered by the delayed release components of compositions of the present invention (i.e., the delayed pulsed release and/or the sustained release components) would be lost (i.e., not absorbed) in the colon. The FDA package insert and labeling for ADDERALL XR® (Shire US, Inc.) are hereby incorporated by reference in their entirety.

Preferred amphetamine salts are those in ADDERALL XR®, i.e., dextroamphetamine sulfate, dextroamphetamine saccharate, amphetamine aspartate monohydrate and amphetamine sulfate. However, the invention is not limited to these salts. Other amphetamines and amphetamine salts can be used in the pharmaceutical compositions of the present invention including, for example, amphetamine base, chemical and chiral derivatives thereof; other amphetamine salts; and mixtures of the foregoing.

The three components comprising the extended release amphetamine composition of the invention release doses of the active ingredients at varying, pre-determined times to provide for full day treatment (i.e., about 14 hours to about 16 hours) of conditions such as ADHD. A treatment for ADHD, which can be delivered in a single dosage is especially beneficial to adolescents and adults who typically have longer daily waking hours compared to children.

The compositions of the present invention comprise an immediate release component, a delayed pulsed release component, and a sustained release component. In embodiments of the invention, delayed pulsed release and/or sustained release can be provided by an enteric coating.

In a particular embodiment, the immediate release component, delayed pulsed release component and sustained release component each contain equal amounts of active ingredient.

In one embodiment, the immediate release, delayed pulsed release and sustained release components of the composition are present on the same core. In another embodiment, the immediate release and delayed pulsed release components are present on different cores. In a further embodiment, the delayed pulsed release and sustained release components are present on different cores. In a preferred embodiment, the immediate release, delayed pulsed release and sustained release components are present on different cores. See FIG. 3.

In yet another embodiment, the amphetamine salt is coated onto a core. In a further embodiment, the amphetamine salt is incorporated into a core.

It is contemplated that compositions of the present invention can include a combination of the hereinabove referred to cores (one or more cores that include three components on the same core, one or more cores that include two of the three components on the core, and one or more cores that include one of the three components on the core).

In an embodiment of the present invention, a pharmaceutical composition is provided in which there is immediate release of drug, a delayed pulsed release of drug, and a sustained release of drug, and wherein the drug includes one or more amphetamine salts and mixtures thereof. In a preferred embodiment, the delayed pulsed release of drug begins about one hour after oral administration of the composition to a patient in the fasted state and the sustained release of drug begins about four hours to about six hours after oral administration to a patient in the fasted state.

Surprisingly, amphetamine salt pharmaceutical compositions of the present invention deliver about bioequivalent drug levels to a patient in either a fasted state or fed state. Thus, an amphetamine salt composition according to the present invention does not exhibit a food effect. This is surprising because it would be expected that some of the drug delivered by delayed release would be released earlier in the presence of food (especially fatty food) due to the increase in gastric pH that accompanies the ingestion of food.

A pharmaceutical composition according to the present invention includes:
  (a) an immediate release bead comprising an amphetamine salt;
  (b) a first delayed release bead comprising an amphetamine salt; and
  (c) a second delayed release bead comprising an amphetamine salt;
wherein the first delayed release bead provides pulsed release of the mixed amphetamine salt and the second delayed release bead provides sustained release of the mixed amphetamine salt.

A pharmaceutical composition of the present invention provides a patient with at least about 14 hours to about 16 hours of effective therapy for Attention Deficit Hyperactivity Disorder (ADHD).

In an embodiment of the invention, the d-amphetamine $C_{max}$ after administration of a 37.5 mg amphetamine pharmaceutical composition to a human patient is about 50 ng/ml.

In another embodiment, the d-amphetamine area under the curve from time 0 to the last measured time ($AUC_{0-last}$) after administration of a 37.5 mg amphetamine pharmaceutical composition to a human patient is about 1058 ng·hr/ml.

Further, according to an embodiment of the present invention, the d-amphetamine area under the curve from time 0 to time infinity ($AUC_{0-inf}$) after administration of a 37.5 mg amphetamine pharmaceutical composition to a human patient is about 1085 ng·hr/ml.

In an embodiment, the present invention provides a pharmaceutical composition, wherein the d-amphetamine $T_{max}$ is about 8.2 hours after administration of a 37.5 mg amphetamine pharmaceutical composition to a human patient.

In a particular embodiment, the l-amphetamine $C_{max}$ after administration of a 37.5 mg amphetamine pharmaceutical composition to a human patient is about 15 ng/ml.

In a further embodiment, the l-amphetamine area under the curve from time 0 to the last measured time ($AUC_{0-last}$) after administration of a 37.5 mg amphetamine pharmaceutical composition to a human patient is about 354 ng·hr/ml.

In another embodiment, the l-amphetamine area under the curve from time 0 to time infinity ($AUC_{0-inf}$) after administration of a 37.5 mg amphetamine pharmaceutical composition to a human patient is about 373 ng·hr/ml.

Further, in an embodiment of the present invention, the l-amphetamine $T_{max}$ is about 8.4 hours after administration of a 37.5 mg amphetamine pharmaceutical composition to a human patient.

In a further embodiment, a protective layer is provided over at least one enteric coating. In another embodiment, a protective layer is provided between the amphetamine salt and at least one enteric coating. A protective layer can also be provided over the sustained release coating according to the present invention.

In a particular embodiment, the amphetamine salt is selected from the group consisting of dextroamphetamine sulfate, dextroamphetamine saccharate, amphetamine aspartate monohydrate, amphetamine sulfate, and mixtures thereof.

In a more particular embodiment, the amphetamine salt is a mixture of dextroamphetamine sulfate, dextroamphetamine saccharate, amphetamine aspartate monohydrate, and amphetamine sulfate.

In an aspect of the present invention, the pharmaceutical composition does not exhibit a food effect.

The present invention encompasses methods for treating ADHD, which comprise administering the amphetamine salt pharmaceutical composition of the present invention to a patient suffering from ADHD.

The delayed pulsed release and sustained release components retard or delay the release of the pharmaceutically active ingredient(s) for a specified time period ("lag time") until a predetermined time. For example, a delayed pulsed release component having an enteric coating layer retards or delays the release of the pharmaceutical active or drug for a lag time, then releases the drug rapidly and completely, i.e., a pulsed release. In one embodiment of a delayed pulsed release, the entire dose is released within about 30-60 minutes following a lag time after administration of the composition. In another example, a sustained release component having an enteric release coating retards or delays the release of the pharmaceutical active or drug for a lag time and then the release of the drug is sustained (i.e., release of the entire dose takes greater than about 60 minutes).

The delay or lag time will take into consideration factors such as transit times, food effects, inflammatory bowel disease, use of antacids or other medicaments, which can alter the pH of the GI tract.

According to the present invention, the lag time for the delayed pulsed release component can be pH dependent or pH independent. In an embodiment of the invention, the lag time for the delayed pulsed release component is only time-dependent, i.e., pH independent. In a preferred embodiment, the lag time is pH dependent.

According to the present invention, a lag time can be about 1 hour to about 14 hours. Multiple dose formulations can have more than one lag time. In a preferred embodiment, the delayed pulsed release component has a lag time of about 60 minutes and the sustained release component has a lag time of about 4 to about 6 hours.

In one aspect, the present invention is directed to a composition that provides for enteric release of at least one pharmaceutically active amphetamine salt, including at least one pharmaceutically active amphetamine salt that is coated with an enteric coating wherein (1) the enteric release coating has a defined minimum thickness and/or (2) there is a protective layer between the at least one pharmaceutically active amphetamine salt and the enteric release coating and/or (3) there is a protective layer over the enteric release coating.

In attempting to provide for delayed pulsed release of an amphetamine salt, applicants found that use of an enteric release coating as generally practiced in the art did not provide the desired release profile. Using the typical amount of enteric coating (10 to 15 wt %) for the delayed pulsed release component resulted in undesired premature leakage of the drug from the delivery system into the upper gastrointestinal tract, and drug delivery at the desired, more distal location in the gastrointestinal tract was reduced. Thus, this coating did not meet the requirements for a drug release profile, which provides full beneficial therapeutic activity at the desired time.

Applicants found that using a thicker application of enteric coating on the delayed pulsed release component allowed for the delayed release pulsed dose to be released only, and completely, at the appropriate time in the desired predetermined area of the gastrointestinal tract, i.e., in the intestine.

This was surprising because an increase in enteric coating thickness above a minimum thickness of about 5 to 10 wt % typically does not have a significant effect on release of drug from within such coatings. Typically, application of a thicker coating (greater than 15 wt %) will only marginally increase the time i.e., for a brief period of time (about 20 minutes) for complete release at the appropriate environmental condition (e.g., the appropriate pH for a pH dependent coating) or appropriate time after ingestion (e.g., when a pH independent coating is used). Using the typical coating, applicants could not achieve the desired delayed pulsed release—rather, the coating leaked before the predetermined time in an inappropriate environment resulting in significant loss of the therapeutic agent.

Accordingly, in one aspect, the pulsed enteric release of the amphetamine salts is accomplished by employing a certain minimum thickness of the enteric coating, i.e., a coating weight percent of about 24 to about 30 wt %.

In one embodiment of the invention, the pulsed dose delivery comprises a multi-layered composition which comprises (1) one or more amphetamine salts; (2) an enteric coating over the one or more amphetamine salts; (3) a sustained release coating over the enteric coating; (4) a second application (e.g., a layer) of amphetamine salts over the sustained release coating; (5) a second enteric coating over the one or more pharmaceutically active amphetamine salts; (6) a third application (e.g., layer) of one or more amphetamine salts over the second enteric coating layer; and an immediate release layer coating.

In one aspect, the one or more amphetamine salts can be provided within or as a part of a core seed around which the sustained release enteric coating is applied. Alternatively, a core seed can be coated with one or more layers of one or more amphetamine salts.

It has further been discovered that a delayed pulsed release drug delivery can also be accomplished by coating the drug first with a protective layer prior to applying the delayed pulsed release enteric coating.

Thus, in another embodiment, the delayed pulsed enteric release is accomplished by employing a protective layer between the drug and the delayed pulsed release enteric coating. In another embodiment, the pulsed enteric release is accomplished by employing a protective layer between drug and the sustained release enteric coating. When using a protective coating, the delayed pulsed release enteric coating or the sustained release enteric coating may be of an increased thickness or may be of lower thickness.

In one aspect of the invention, the protective layer is comprised of one or more components, which includes an immediate release layer and a modifying layer. The modifying layer is preferably comprised of a semi water-permeable polymer. Applicants have found that a semi-permeable polymer coating used in combination with an immediate release layer coating provided a delayed pulsed release drug delivery profile when layered over the enteric coating.

Thus, in this embodiment, the protective layer comprises a semi-permeable polymer and an immediate release coating layer. In a further embodiment, the modifying layer comprises a first layer of a semi-permeable polymer which is adjacent to the enteric coating layer and a second coating layer over the semi-permeable polymer coating layer comprising an immediate release polymer coating layer.

In one aspect of this embodiment, a semi-permeable polymer, which may comprise a low water-permeable pH-insensitive polymer, is layered onto the outer surface of the enteric layer, in order to obtain prolonged delayed release time. This semi-permeable polymer coating controls the erosion of the pH-sensitive enteric polymer in an alkaline pH environment in which a pH-sensitive polymer will dissolve rapidly. Another pH-sensitive layer may be applied onto the surface of a low water-permeability layer to further delay the release time.

In a still further aspect of the invention, in addition to a protective layer, the composition comprises an acid which is incorporated into the pharmaceutical active layer or coated onto the surface of the active layer to reduce the pH value of the environment around the enteric polymer layer. The acid layer may also be applied on the outer layer of the pH-sensitive enteric polymer layer, followed by a layer of low water-permeability polymer. The release of the active ingredient thus may be delayed and the dissolution rate may be increased in an alkaline environment.

In a further embodiment, the protective coating may be used both over the drug and over the enteric coating.

With respect to this embodiment of the invention, the one or more amphetamine salts can be provided within or as a part of a core seed, during the core seed manufacturing process, around which the enteric coating is applied. Alternatively, a core seed can be coated with one or more layers of one or more amphetamine salts.

Compositions of the present invention encompass mixed amphetamine salt dosages of about 10 mg to about 100 mg. In an embodiment of the present invention, the pharmaceutical composition comprises a mixed amphetamine salt dosage of about 12.5 mg. In further embodiments of the present invention, the pharmaceutical composition comprises a mixed amphetamine salt dosage of about 18.75 mg, about 25 mg, about 31.25 mg, about 37.5 mg, about 43.75 mg, about 50 mg, about 62.5 mg, and about 75 mg. Dissolution profiles for 12.5 mg, 25 mg, 37.5 mg and 50 mg compositions of the invention are provided in FIGS. 4-7, respectively.

The drug delivery system of the present invention as described herein preferably comprises one or a number of beads or beadlets in a dosage form, either capsule, tablet, sachet or other method of orally administering the beads. In a specific embodiment of the present invention, the drug delivery system comprises three beads or beadlets in a dosage form, either capsule, tablet, sachet or other method of orally administering the beads. In a preferred embodiment, the immediate release beads, the delayed pulsed release beads, and the sustained release beads are present in the composition in an about 1:1:1 ratio.

DETAILED DESCRIPTION OF THE INVENTION

Figure 1:
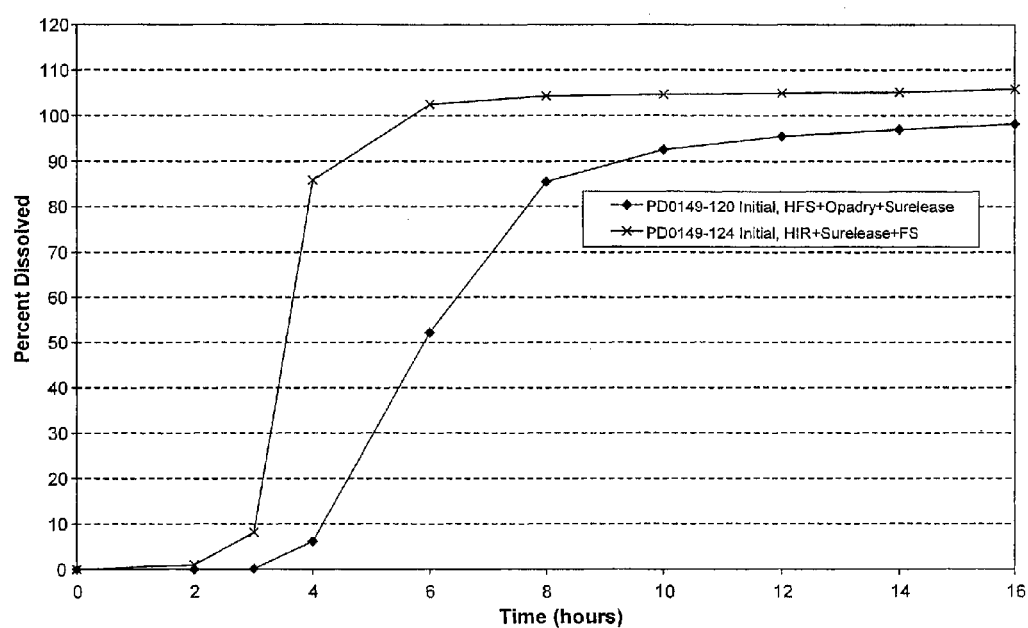
FIG. 1, is a graph showing the dissolution profiles for a typical sustained release formulation (PD0149-124) and a sustained release formulation of the present invention (PD0149-120). HFS is the formulation exemplified in Example 2, infra; HIR is the formulation exemplified in Example 1, infra; and FS is EUDRAGIT® FS30 D.
Figure 2:
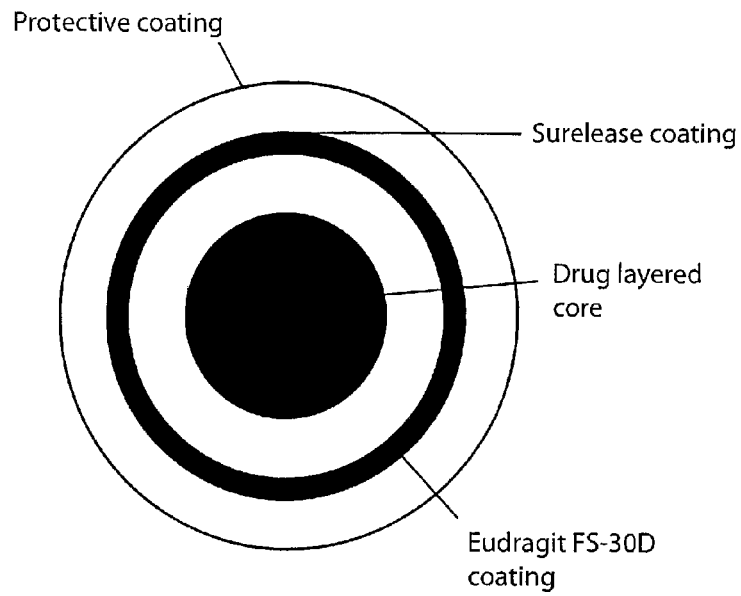
FIG. 2 illustrates the construction of the sustained release bead.
Figure 3:
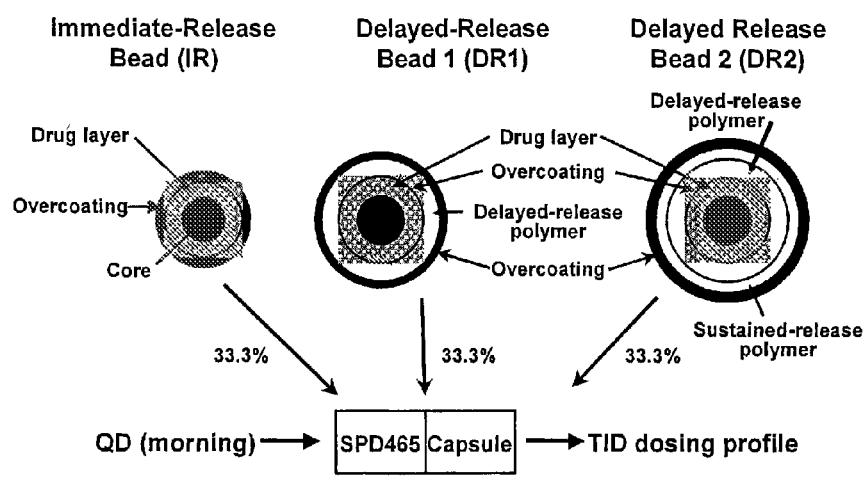
FIG. 3 illustrates a 3-bead controlled dose drug delivery system of the present invention, including an immediate release component (IR bead), a delayed pulsed release component (DR1 bead) and a sustained release component (DR2 bead).
Figure 4:
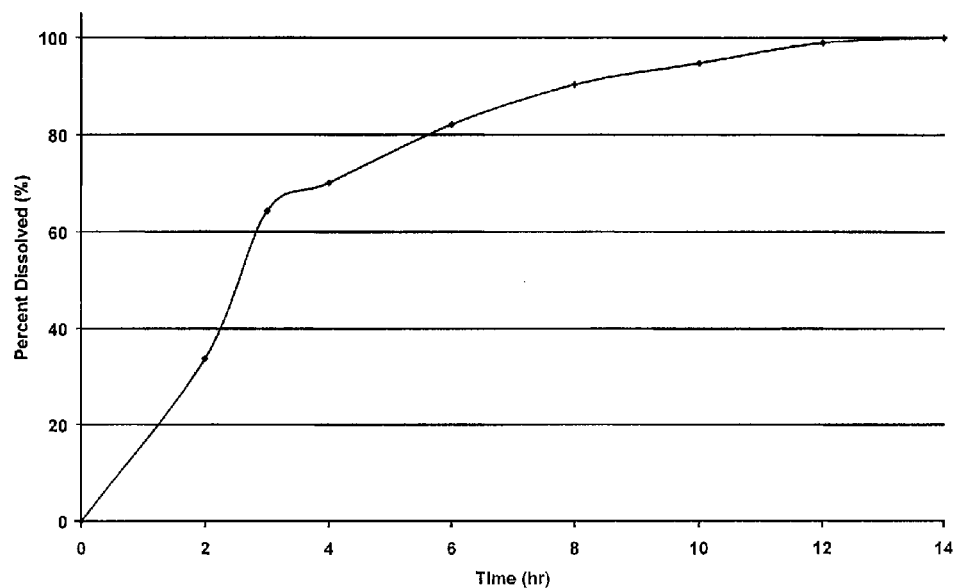
FIG. 4 is a graph showing the dissolution profile of a 12.5 mg mixed amphetamine salt 3-bead composition according to the invention.

Various types of controlled drug release and release profiles are contemplated by the present invention.

The terms "bead" and "pellet" refer to a discrete component of a dosage form. For example, a capsule shell is filled with a plurality of beads or pellets. As used herein, bead and pellet encompass any discrete component of a dosage form.

"Immediate" and "delayed" release refer to the onset of release in relationship to administration of the drug. "Immediate" means that the release of drug begins very soon, within a relatively short time after administration, e.g. a few minutes or less. "Delayed" means that the release of drug is postponed, and begins or is triggered some period of time after administration (e.g., the lag time), typically a relatively long period of time, e.g. more than one hour.

"Rapid" and "slow" release refer to the rate of release after onset. Once delivery of the drug begins, it may be released relatively quickly or relatively slowly. A rapid release indicates that, after onset, a maximum or peak dose is reached in a relatively short period of time. A slow release indicates that, after onset, a maximum or peak dose is reached in a relatively long period of time. Once reached, the maximum dose may fall off at any pace (e.g. fast, slow, or constant).

"Sustained" or "continuous" refers to the period of ongoing release, and means that the delivery of drug goes on (it continues or is sustained) for an extended period of time after initial onset, typically more than one hour, whatever the shape of the dose release profile. For example, the drug release is sustained between a maximum and minimum value (more than zero) for some relatively long period of time. This release may be at a constant dose, or at a dose which diminishes over time.

"Constant" release refers to the dose that is being released, and means that a drug is delivered at a relatively constant dose over a moderate or extended period of time. This can be represented by a dose release profile that is relatively flat or only gently sloped after initial onset, i.e. without highly distinct peaks and valleys. Thus, a constant release will typically be sustained or continuous, but a sustained or continuous release may not be constant.

"Pulsed" release means that a drug is delivered in one or more doses that fluctuate between a maximum and minimum dose over a period of time. This can be represented by a dose release profile having one or more distinct peaks or valleys. However, two or more pulsed releases may produce an overlapping, overall, or composite release profile that appears or effectively is constant. When two or more pulsed releases occur, there may or may not be a period of no release between pulses. Typically, pulsed release results in release of essentially all of a drug within about 60 minutes or less.

"Extended" release refers to a formulation which provides either a release of drug within a targeted dose range for a relatively long period, or a plasma level of drug within a targeted dose range for a relatively long period, without regard for the particular mechanism or character of release, e.g. as sustained, pulsed, or constant.

"Effective therapy" or "effective treatment," as used herein, means to prevent, alleviate, arrest, or inhibit at least one symptom or sign of ADHD. Symptoms and signs of ADHD include, for example, inattention, hyperactivity and impulsivity.

"Food effect," as used herein, means a significant difference in the bioavailability of a drug in a patient when the drug is administered in a fasted state compared to a fed state. "No food effect" means that there is no significant difference in the bioavailability of a drug in a patient when the drug is administered in a fasted state compared to a fed state.

The term "about" or "approximately" means within an acceptable error range for the particular value as determined by one of ordinary skill in the art, which will depend in part on how the value is measured or determined, i.e., the limitations of the measurement system, i.e., the degree of precision required for a particular purpose, such as a pharmaceutical formulation. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

Drug release and drug release profiles are measures or representations of the manner and timing by which a formulation releases or delivers active ingredients (drug) to a receiving environment (e.g. the stomach, intestines, etc.) upon administration. Various methods are known for evaluating drug release and producing release profiles, including in vitro tests which model the in vivo behavior of a formulation. These include USP dissolution testing for immediate release and controlled release solid dosage forms.

Drug release profiles are distinct from plasma profiles. A plasma profile is a measure or representation of the dose or level of active ingredient (drug) in the bloodstream of a mammal, e.g. a patient receiving a drug formulation. Upon release of a drug from a formulation, e.g. into the gut of a mammal, the amount of drug that is present in the bloodstream over time can be determined.

A drug release profile may be designed to produce a desired or targeted plasma profile. Often, but not necessarily, a plasma profile will mimic a release profile. For example, it might be expected that a sustained release of drug would more likely produce a sustained dose in the plasma, or that a pulsed release would produce a pulsed (peak and valley) plasma profile. This is not necessarily so, however. For example, the half-life of the drug in the blood stream (its rate of decay) may be such that a sustained or continuous plasma profile could result from a pulsed delivery profile. Other factors may also play a role, such as bio-absorption, bioavailability, and first pass effect. The plasma profile produced by a particular release profile may also vary from patient to patient.

Measures of bioavailability well known in the art include the area under the plasma concentration-time curve (AUC), the concentration maximum ($C_{max}$), and the time to $C_{max}$ ($T_{max}$).

AUC is a measurement of the area under the plasma concentration-time curve, and is representative of the amount of drug absorbed following administration of a single dose of a drug (Remington: The Science and Practice of Pharmacy, (Alfonso R. Gennaro ed. 2000), page 999).

$C_{max}$ is the maximum plasma concentration achieved after oral drug administration (Remington, page 999). An oral drug administration results in one $C_{max}$, but may result in greater than one "peak plasma concentration" or "plasma concentration peak" (for example, following the administration of a pulsed dose formulation).

$T_{max}$ is the amount of time necessary to achieve the $C_{max}$ after oral drug administration, and is related to the rate of absorption of a drug (Remington, page 999).

Bioequivalence is the absence of a significantly different rate and extent of absorption in the availability of the active ingredient when administered at the same dose under similar conditions. Bioequivalence can be measured by pharmacokinetic parameters such as, for example, AUC and Cmax.

A drug delivery system of the invention typically may comprise a core seed or matrix, which may or may not be loaded with drug, and one or more coating layers comprising drug, and/or comprising a layer have release characteristics which control the onset and release characteristics of the drug. An exemplary core is a sugar core. Exemplary matrixes include hydrophilic matrixes. Polymers useful for forming a hydrophilic matrix include hydroxypropyl methylcellulose (HPMC), hydroxypropyl cellulose (HPC), poly(ethylene oxide), poly(vinyl alcohol), xanthan gum, carbomer, carrageenan, and zooglan. Other similar hydrophilic polymers may also be employed.

Coating layers can provide immediate release, delayed pulsed release or sustained release. Immediate release of the drug from the immediate-release layer can be achieved by any of various methods known in the art. One example is the use of a very thin layer or coating which by virtue of its thinness is quickly penetrated by gastric fluid allowing rapid leaching of the drug. Another example is by incorporating the drug in a mixture that includes a supporting binder or other inert material that dissolves readily in gastric fluid, releasing the drug as the material dissolves. A third is the use of a supporting binder or other inert material that rapidly disintegrates upon contact with gastric fluid, with both the material and the drug quickly dispersing into the fluid as small particles. Examples of materials that rapidly disintegrate and disperse are lactose and microcrystalline cellulose. An example of a suspending agent and binder is hydroxypropyl methylcellulose.

Enteric coatings for the delayed pulsed release component can be pH-dependent or pH-independent. Enteric coatings for the sustained release component are pH dependent. A pH dependent coating is activated to release drug within a known pH range, which typically is matched to the local pH of the environment where delayed release is desired. Exemplary pH dependent coatings include cellulose acetate phthalate, cellulose acetate trimellitate, hydroxypropyl methylcellulose phthalate, polyvinyl acetate phthalate, carboxymethylethylcellulose, co-polymerized methacrylic acid/methacrylic acid methyl esters such as, for instance, materials known under the trade name EUDRAGIT® L12.5, L100, or EUDRAGIT® S12.5, S100 or similar compounds used to obtain enteric coatings. Aqueous colloidal polymer dispersions or re-dispersions can be also applied, e.g. EUDRAGIT® L 30D-55, EUDRAGIT® L100-55, EUDRAGIT® S100, EUDRAGIT® preparation 4110D (Rohm Pharma); AQUATERIC®, AQUACOAT® CPD 30 (FMC); KOLLICOAT MAE® 30D and. 30DP (BASF); EASTACRYL® 30D (Eastman Chemical).

A pH independent coating includes materials susceptible to enzymatic activation by azo-reductases in intestinal bacteria (i.e., azo-polymers) or materials susceptible to degradation by polysaccaridases in the colon (natural polysaccarides). Non-limiting examples of azo-polymers include co-polymers of 2-hydroxyethyl methacrylate (HEMA) and methyl methacrylate (MMA). Non-limiting examples of natural polysaccharides include amylose, chitosan, chrondoitin, dextran, and xylan.

The sustained release component can include sustained release coatings, sustained release matrices, and sustained release osmotic systems. Sustained release coatings can be prepared using a water-insoluble polymer, a combination of water-insoluble polymers, or a combination water-insoluble and water-soluble polymers. Conventional sustained release polymers well known to those of ordinary skill in the formulary arts can be used for the sustained release matrix.

Exemplary sustained release coatings can include polyvinyl acetate, cellulose acetate, cellulose acetate butyrate, cellulose acetate propionate, ethyl cellulose, fatty acids and esters thereof, alkyl alcohols, waxes, zein (prolamine from corn), and aqueous polymeric dispersions such as EUDRAGIT® RS and RL30D, EUDRAGIT® NE30D, AQUACOAT®, SURELEASE®, KOLLICOAT® SR30D, and cellulose acetate latex.

Principles of sustained release formulation technology applicable to this invention, include those disclosed in R. K. Chang and J. R. Robinson, chapter 4: "Sustained Drug Release from Tablets and Particles Through Coating," in Pharmaceutical Dosage Forms: Tablets, volume 3, edited by H. A. Lieberman, L. Lachman, and J. B. Schwartz, Marcel Dekker, Inc., 1991; R. J. Campbell and G. L. Sackett, chapter 3: "Film coating," in Pharmaceutical Unit Operations: Coating, edited by K. E. Avis, A. J. Shukla, and R. K. Chang, Interpharm Press, Inc., 1999.

The present invention comprises a core or starting seed, either a prepared or commercially available product. The cores or starting seeds can be sugar spheres, spheres made from microcrystalline cellulose and any suitable drug crystals.

The materials that can be employed in making drug-containing pellets are any of those commonly used in pharmaceutics and should be selected on the basis of compatibility with the active drug and the physicochemical properties of the pellets. The additives except active drugs are chosen below as examples:

Binders such as cellulose derivatives such as methylcellulose, hydroxyethyl cellulose, hydroxypropyl cellulose, hydroxypropyl methylcellulose, polyvinylpyrrolidone, polyvinylpyrrolidone/vinyl acetate copolymer and the like.

Disintegration agents such as corn starch, pregelatinized starch, cross-linked carboxymethylcellulose (AC-DI-SOL®), sodium starch glycolate (EXPLOTAB®), cross-linked polyvinylpyrrolidone (PLASDONE XL®), and any disintegration agents used in tablet preparations.

Filling agents such as lactose, calcium carbonate, calcium phosphate, calcium sulfate, microcrystalline cellulose, dextran, starches, sucrose, xylitol, lactitol, mannitol, sorbitol, sodium chloride, polyethylene glycol, and the like.

Surfactants such as sodium lauryl sulfate, sorbitan monooleate, polyoxyethylene sorbitan monooleate, bile salts, glyceryl monostearate, PLURONIC® line (BASF), and the like.

Solubilizers such as citric acid, succinic acid, fumaric acid, malic acid, tartaric acid, maleic acid, glutaric acid sodium bicarbonate and sodium carbonate and the like.

Stabilizers such as any antioxidation agents, buffers, acids, and the like, can also be utilized.

Methods of manufacturing the core include a. Extrusion-Spheronization—Drug(s) and other additives are granulated by addition of a binder solution. The wet mass is passed through an extruder equipped with a certain size screen. The extrudates are spheronized in a marumerizer. The resulting pellets are dried and sieved for further applications.

b. High-Shear Granulation—Drug(s) and other additives are dry-mixed and then the mixture is wetted by addition of a binder solution in a high shear-granulator/mixer. The granules are kneaded after wetting by the combined actions of mixing and milling. The resulting granules or pellets are dried and sieved for further applications.

c. Solution or Suspension Layering—A drug solution or dispersion with or without a binder is sprayed onto starting seeds with a certain particle size in a fluid bed processor or other suitable equipment. The drug thus is coated on the surface of the starting seeds. The drug-loaded pellets are dried for further applications.

For purposes of the present invention, the core particles have a diameter in the range of about 50-1500 microns; preferably 100-800 microns.

These particles can then be coated in a fluidized bed apparatus with an alternating sequence of coating layers.

The core may be coated directly with a layer or layers of at least one pharmaceutically active amphetamine salts and/or the pharmaceutically active amphetamine salt may be incorporated into the core material. Pharmaceutically active amphetamine salts contemplated to be within the scope of the present invention include amphetamine base and salts thereof. Preferred pharmaceutically active amphetamine salts include dextroamphetamine sulfate, dextroamphetamine saccharate, amphetamine aspartate monohydrate and amphetamine sulfate.

A protective layer may be added on top of the pharmaceutical active containing layer and also may be provided between active layers. A separation or protective layer may be added onto the surface of the active-loaded core, and then the enteric delayed pulsed or sustained release layer is coated thereupon. Another active layer may also be added to the enteric delayed pulsed or sustained layer to deliver an initial dose.

A protective coating layer may be applied immediately outside the core, either a drug-containing core or a drug-layered core, by conventional coating techniques such as pan coating or fluid bed coating using solutions of polymers in water or suitable organic solvents or by using aqueous polymer dispersions. Suitable materials for the protective layer include cellulose derivatives such as hydroxyethyl cellulose, hydroxypropyl cellulose, hydroxypropyl methylcellulose, polyvinylpyrrolidone, polyvinylpyrrolidone/vinyl acetate copolymer, ethyl cellulose aqueous dispersions (AQUACOAT®, SURELEASE®), EUDRAGIT® RL 30D, OPADRY® and the like. The suggested coating levels are from 1 to 6%, preferably 2-4% (w/w).

The enteric delayed pulsed release or sustained release coating layer is applied onto the cores with or without seal coating by conventional coating techniques, such as pan coating or fluid bed coating using solutions of polymers in water or suitable organic solvents or by using aqueous polymer dispersions. Suitable coaters are well known in the art. For example, any commercially available pH-sensitive polymer can be used. With such a polymer, the pharmaceutical active is not released in the acidic stomach environment of approximately below pH 4.5, but is not limited to this value. The pharmaceutical active should become available when the pH-sensitive layer dissolves at the greater pH; after a certain delayed time; or after the unit passes through the stomach.

Suitable enteric polymers for the delayed pulsed release component and sustained release component include, for example, cellulose acetate phthalate, cellulose acetate trimellitate, hydroxypropyl methylcellulose phthalate, polyvinyl acetate phthalate, carboxymethylethylcellulose, co-polymerized methacrylic acid/methacrylic acid methyl esters such as, for instance, materials known under the trade name EUDRAGIT® L12.5, L100, or EUDRAGIT® S12.5, S100 or similar compounds used to obtain enteric coatings. Aqueous colloidal polymer dispersions or re-dispersions can be also applied, e.g. EUDRAGIT® L 30D-55, EUDRAGIT® L100-55, EUDRAGIT® S100, EUDRAGIT® preparation 4110D (Rohm Pharma); AQUATERIC®, AQUACOAT® CPD 30 (FMC); KOLLICOAT MAE® 30D and. 30DP (BASF); EASTACRYL® 30D (Eastman Chemical).

The enteric delayed pulsed release and sustained release polymers used in this invention can be modified by mixing with other known coating products that are not pH sensitive. Examples of such coating products include the neutral methacrylic acid esters with a small portion of trimethylammonioethyl methacrylate chloride, sold currently under the trade names EUDRAGIT® RS and EUDRAGIT® RL; a neutral ester dispersion without any functional groups, sold under the trade names EUDRAGIT® NE30D; and other pH independent coating products.

The modifying component of the protective layer used over the enteric delayed pulsed release or sustained release coating can include a water penetration barrier layer (semipermeable polymer) which can be successively coated after the enteric coating to reduce the water penetration rate through the enteric coating layer and thus increase the lag time of the drug release. Coatings commonly known to one skilled in the art can be used for this purpose and applied by conventional techniques such as pan coating or fluid bed coating using solutions of polymers in water or suitable organic solvents or by using aqueous polymer dispersions. For example, the following materials can be used, but not limited to: cellulose acetate, cellulose acetate butyrate, cellulose acetate propionate, ethyl cellulose, fatty acids and their esters, waxes, zein, and aqueous polymer dispersions such as EUDRAGIT® RS and RL 30D, EUDRAGIT® NE 30D, AQUACOAT®, SURELEASE®, cellulose acetate latex. The combination of above polymers and hydrophilic polymers such as hydroxyethyl cellulose, hydroxypropyl cellulose (KLUCEL®, Hercules Corp.), Hydroxypropyl methylcellulose (METHOCEL®, Dow Chemical Corp.). Polyvinylpyrrolidone can also be used.

An overcoating layer can further optionally be applied to the composition of the present invention: OPADRY®, OPADRY II® (Colorcon) and corresponding color and colorless grades from Colorcon can be used to protect the pellets from being tacky and provide colors to the product. The suggested levels of protective or color coating are from 1 to 6%, preferably 2-3% (w/w). Talc can also be used for this purpose, e.g., a 2% w/w talc treatment can be applied.

Many ingredients can be incorporated into the overcoating formula, for example to provide a quicker immediate release, such as plasticizers: acetyltriethyl citrate, triethyl citrate, acetyltributyl citrate, dibutylsebacate, triacetin, polyethylene glycols, propylene glycol and the others; lubricants: talc, colloidal silica dioxide, magnesium stearate, calcium stearate, titanium dioxide, magnesium silicate, and the like.

The composition, preferably in beadlet form, can be incorporated into hard gelatin capsules, either with additional excipients, or alone. Typical excipients to be added to a capsule formulation include, but are not limited to: fillers such as microcrystalline cellulose, soy polysaccharides, calcium phosphate dihydrate, calcium sulfate, lactose, sucrose, sorbitol, or any other inert filler. In addition, there can be flow aids such as fumed silicon dioxide, silica gel, magnesium stearate, calcium stearate or any other material imparting flow to powders. A lubricant can further be added if necessary by using polyethylene glycol, leucine, glyceryl behenate, magnesium stearate or calcium stearate.

The composition can be incorporated into a tablet, in particular by incorporation into a tablet matrix, which rapidly disperses the particles after ingestion. In order to incorporate these particles into such a tablet, a filler/binder must be added to a table that can accept the particles but will not allow their destruction during the tableting process. Materials that are suitable for this purpose include, but are not limited to, microcrystalline cellulose (AVICEL®), soy polysaccharide (EMCOSOY®), pre-gelatinized starches (STARCH® 1500, NATIONAL® 1551), and polyethylene glycols (CARBOWAX®). The materials should be present in the range of 5-75% (w/w), with a preferred range of 25-50% (w/w).

In addition, disintegrants are added in order to disperse the beads once the tablet is ingested. Suitable disintegrants include, but are not limited to: cross-linked sodium carboxymethyl cellulose (AC-DI-SOL®), sodium starch glycolate (EXPLOTAB®, PRIMOJEL®), and cross-linked polyvinylpolypyrrolidone (Plasone-XL). These materials should be present in the rate of 3-15% (w/w), with a preferred range of 5-10% (w/w).

Lubricants can be added to assure proper tableting, and these can include, but are not limited to: magnesium stearate, calcium stearate, stearic acid, polyethylene glycol, leucine, glyceryl behenate, and hydrogenated vegetable oil. These lubricants should be present in amounts from 0.1-10% (w/w), with a preferred range of 0.3-3.0% (w/w).

Tablets are formed, for example, as follows. The particles are introduced into a blender along with AVICEL®, disintegrants and lubricant, mixed for a set number of minutes to provide a homogeneous blend which is then put in the hopper of a tablet press with which tablets are compressed. The compression force used is adequate to form a tablet; however, not sufficient to fracture the beads or coatings.

A tablet according to the present invention can be constructed in three layers, wherein the immediate release component is dry blended, and the delayed pulsed release and the sustained release components are wet granulated. The tablet is then formed in a one layer or a three layer compression. Upon dissolution of the layers in the one layer or three layer tablet, each component is released and acts in its own way (i.e., the immediate release particles provide immediate release, the delayed pulsed release particles provide delayed pulsed release, and the sustained release particles provide sustained release after a lag time).

It will be appreciated that the multiple dosage form of the present invention can deliver rapid and complete dosages of pharmaceutically active amphetamine salts to achieve the desired levels of the drug in a recipient over the course of about 14 hours to about 16 hours with a single oral administration.

This invention also encompasses the use of a longer-day amphetamine composition to treat conditions other than ADHD. These conditions include, but are not limited to, Alzheimer's disease and other memory disorders, fibromyalgia, chronic fatigue, depression, obsessive compulsive disorder, alone or in combination with a SSRI; oppositional defiant disorder (ODD), with or without ADHD and with or without any compositions or formulations of guanfacine or buproprion; anxiety, with or without ADHD and alone or in combination with an anxiolytic or SSRI; resistant depression; stroke rehabilitation; Parkinson's disease; mood disorder; schizophrenia; Huntington's disorder; dementia, e.g. AIDS dementia and frontal lobe dementia; movement dysfunction; apathy; fatigue; Pick's disease; sleep disorders, e.g., narcolepsy, cataplexy, sleep paralysis and hypnagogic hallucinations; etc.

The invention also contemplates combinations of the longer-day amphetamine compositions of this invention with other therapeutic agents. The drugs can be formulated in the same dosage form as the longer-day amphetamine composition dose of the invention or can be formulated separately, in which case, the drugs can be administered sequentially in any order or simultaneously. Typically, dosages can be in the same ranges as for each drug used separately or, where synergistic effects occur, one or more of the combined drugs can be used in lower dosages.

The other therapeutic agents can include e.g., for Alzheimer's: galanthamine, tacrine, donepezil, rivastigmine, memantine, human growth hormone, selegiline hydrochoride, estrogen, clioquinol, ibuprofen, and Gingko bilboa; for ADHD: methylphenidate (e.g., RITALIN®, CONCERTA®), amphetamine, pemoline, clonidine, guanfacine, etc; for depression: fluoxetine hydrochloride, sertraline HCL, paroxetine HCL, reboxetine, bupropion HCL, olanzapine, fluoxetine hydrochloride, amitriptyline, imipramine, nortriptyline, phenelzine, tranylcypromine sulfate, trazodone, and venlafaxine; for mood disorder: thorazine, haloperidol, thiothixene, thioridazine, risperadone, clozapine, risperidone, and olanzapine; for fatigue: benzodiazepines, naproxen, fluoxetine hydrochloride, sertraline HCL, paroxetine HCL, venlafaxine, and trazodone; for fibromyalgia: phenytoin, carbamazepine, valproate, divalproex, desipramine, nortriptyline, amitryptiline, doxepin, and non-steroidal inflammatory drugs; for oppositional defiant disorder (ODD): clonidine, risperidone, and olanzepine; for apathy: amisulpride, olanzapine, visperidone, quetiapine, clozapine, and zotepine; for Parkinson's disease: levodopa, bromocriptine, pergolide, and pramipexole; for schizophrenia: clozapine, olanzepine, quetiapine fumarate, and risperidone; for Huntington's disorder: haloperidol and clonzepam; for dementia: thioridazine, haloperidol, risperidone, tacrine, donepezil, and rivastigmine; for narcolepsy: modafinil, amphetamine, modafinil and RITALIN®; for cataplexy: sodium oxybate; for hallucinations: clozapine, risperidone, olanzepine, and quetiapine fumarate; for sleep paralysis: PEROCET®, VICODIN®, and LORCET®; for obsessive compulsive disorder: clomipramine, fluoxetine hydrochloride, sertraline HCL, paroxetine HCL, fluvoxamine; and for anxiety: amitryptiline, amoxepine, bupropion HCL, carbamazepine, clomipramine, desipramine, doxepin, imipramine, nortriptyline, VENTYL®, trimipramine etc; selective serotonin reuptake inhibitors (SSRIs) including fluoxetine hydrochloride, fluvoxamine, nefazodone, paroxetine HCL, sertraline HCL venlafaxine, etc., benzodiazepines, including alprazolam, chlordiazepoxide, clonazepam, diazepam, flurazepam, lorazepam, oxazepam, triazolam, etc., monamine oxidase inhibitors including moclobemide, phenelzine, tranylcypromine sulfate, etc.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

The following examples are presented for illustration and do not limit the invention.

EXAMPLES

Example 1

Immediate Release Formulation (HIR)

Sugar sphere seeds (30/35 Mesh, NF) were put into a FLM-15 fluid bed processor with a 9-Wurster column and fluidized at 60° C. A suspension of a mixture containing amphetamine aspartate; amphetamine sulfate, USP; dextroamphetamine saccharate; and dextroamphetamine sulfate, USP with Hypromellose 2910, USP/NF as a binder was sprayed onto the seeds under suitable conditions. After drying, an OPADRY® Beige, YS-1-17274-A seal coating was applied. The ingredients are listed by weight percent in Table 1.

TABLE 1

| Ingredient | Weight % |
| --- | --- |
| Amphetamine aspartate | 4.75 |
| Amphetamine sulfate, USP | 4.75 |
| Dextroamphetamine saccharate | 4.75 |
| Dextroamphetamine sulfate, USP/NF | 4.75 |
| Sugar sphere 30/35 mesh, USP/NF | 78.00 |
| OPADRY® Beige, YS-1-17274-A | 2.00 |
| Hypromellose 2910, USP/NF | 1.00 |
| Purified water, USP | * |
| Total | 100.00 |

* removed during processing

Example 2

Intermediate Formulation (HFS)

The following formulation was used to coat the immediate release mixed amphetamine salt pellets from Example 1 with EUDRAGIT® FS30D (also referred to herein as EUDRAGIT® 4110D) (Rohm Pharma, Germany) coating dispersion. The immediate release pellets of Example 1 were loaded in a fluid bed processor with a reduced Wurster column (GPGC-15, Glatt). The coating dispersion was prepared by dispersing triethyl citrate, USP/NF; talc, USP/NF and EUDRAGIT® FS30D into water and mixing for at least 30 minutes. Under suitable fluidization conditions, the coating dispersion was sprayed onto the fluidized mixed amphetamine salt pellets. The spraying was continued until the targeted coating level of 25-30 weight percent (wt %) was achieved. The coated pellets were dried at 30-35° C. for 5 minutes before stopping the process. After drying, the pellets were coated with OPADRY® Beige, YS-1-17274-A. The ingredients are listed by weight percent in Table 2.

TABLE 2

| Ingredients | Weight (%) |
| --- | --- |
| Immediate release pellets (Example 1) | 65.50 |
| MAA/MA/MMA Copolymer Suspension (EUDRAGIT® FS30 D)* | 27.77 |
| Triethyl citrate, USP/NF | 1.35 |
| Talc, USP/NF | 3.38 |
| OPADRY® Beige, YS-1-17274-A | 2.00 |
| Water | ** |
| Total | 100.00 |

*MAA/MA/MMA Copolymer Suspension is Methyl Acrylate, MethylMethacrylate, and Methacrylic Acid Copolymer (EUDRAGIT® FS30D)
** removed during processing

Example 3

Delayed Release Formulation (HDR)

The following formulation was used to coat the immediate release mixed amphetamine salt pellets from Example 1 with EUDRAGIT® L30 D-55 coating dispersion. The immediate release pellets of Example 1 were loaded in a fluid bed processor with a reduced Wurster column (GPGC-15, Glatt). The coating dispersion was prepared by dispersing Triethyl citrate, USP/NF; Talc, USP/NF and EUDRAGIT® L30D-55 into water and mixing for at least 30 minutes. Under suitable fluidization conditions, the coating dispersion was sprayed onto the fluidized mixed amphetamine salt pellets. The spraying was continued until the targeted coating level of 27-32 weight percent was achieved. The coated pellets were dried at 30-35° C. for 5 minutes before stopping the process. After drying, the pellets were coated with OPADRY® Beige, YS-1-17274-A. The ingredients are listed by weight percent in Table 3.

TABLE 3

| Ingredients | Weight (%) |
| --- | --- |
| Immediate release pellets (Example 1) | 63.00 |
| Methacrylic Acid Copolymer Dispersion, USP/NF (EUDRAGIT® L30 D-55)* | 29.03 |
| Triethyl citrate, USP/NF | 2.94 |
| Talc, USP/NF | 3.04 |
| OPADRY® Beige, YS-1-17274-A | 2.00 |
| Water | ** |
| Total | 100.01 |

*Methacrylic Acid Copolymer Dispersion, USP/NF (EUDRAGIT® L30 D-55) is supplied as a 30% aqueous dispersion.
** removed during processing

Example 4

Sustained Release Formulation (HDR2)

Figure 8:
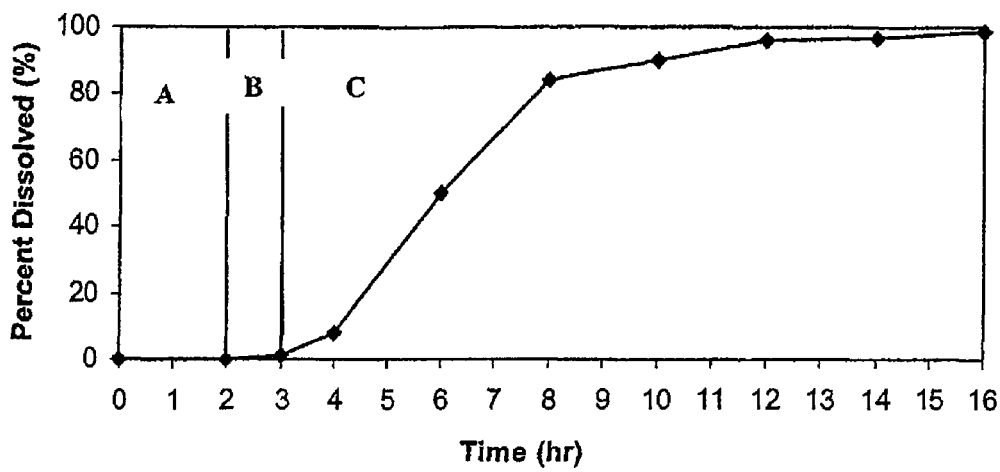
FIG. 8 is a graph showing the dissolution profile of a SPD465 sustained release bead (HDR2). The following pH conditions were used: at 0-2 hours, pH 1.1; at 2-3 hours, pH 6.0; at three hours and greater, pH 7.5.

Intermediate formulation pellets from Example 2 were loaded into a fluid bed processor with a reduced Wurster column (GPGC-15, Glatt). The coating dispersion was prepared by mixing SURELEASE®, talc, USP/NF and water for at least 15 minutes prior to spraying. Under suitable fluidization conditions, the coating dispersion was sprayed onto the fluidized pellets. The spraying was continued until the targeted coating level of 7-9 weight percent of SURELEASE® solids was achieved. The coated pellets were then dried at 35-40° C. for 10 minutes before discharging from the bed. The ingredients are listed by weight percent in Table 4. The dissolution profile for the HDR2 sustained release bead is shown in FIG. 8.

TABLE 4

| Ingredients | Weight (%) |
| --- | --- |
| Intermediate formulation (Example 2) | 90.00 |
| Talc, USP/NF | 2.00 |
| SURELEASE® Clear E-7-19010* | 8.00 |
| Water | ** |
| Total | 100.00 |

*SURELEASE® Clear E-7-19010 is supplied as a 24.5% solids aqueous dispersion
** removed during processing A 12.5 mg mixed amphetamine salt sustained release bead (lot no. B02013) produced according to this Example was administered to 12 subjects aged 18-55 years old and compared to ADDERALL® 10 mg in a crossover study (Clinical Study 101). Two other prototype beads were also tested. A parametric (normal theory) general linear model was applied to the calculation of AUC, Cmax, Tmax and $t_{1/2}$ for each of the formulations. AUC and Cmax were also analyzed on a log scale to assess bioequivalence between test treatments. The results for the sustained release bead and the reference ADDERALL® are shown in Table 5.

TABLE 5

| | AUC (0-inf) (ng · hr/mL) | AUC (0-t) (ng · hr/mL) | Cmax (ng/mL) | Tmax (hr) |
|---|---|---|---|---|
| d-amphetamine | | | | |
| 12.5 mg mixed amphetamine salt sustained release bead | 367.19* | 353.64* | 18.67 | 8.83* |
| 10 mg ADDERALL ® (reference) | 280.59 | 266.70 | 18.62 | 2.17 |
| ratio of test to reference (90% CI) | 1.03 (0.97-1.11)** | 1.05 (0.98-1.12)** | 0.80 (0.76-0.84) | |
| l-amphetamine | | | | |
| 12.5 mg mixed amphetamine salt sustained release bead | 125.23* | 112.44* | 5.64 | 9.33* |
| 10 mg ADDERALL ® (reference) | 100.64 | 87.93 | 5.53 | 2.50 |
| ratio of test to reference (90% CI) | 0.99 (0.91-1.08)** | 1.02 (0.93-1.11)** | 0.81 (0.76-0.87) | |

*$p < 0.05$ compared to 10 mg ADDERALL ®
**90% confidence interval fell within recommended 0.80-1.25 limits of bioequivalence when analyzed on logarithmic scale.

The results of this pharmacokinetic study showed that a single dose of the sustained release formulation had a Tmax significantly longer than a single dose of ADDERALL®. Additionally, the AUCs of the sustained release formulation were equivalent to that of dose-adjusted ADDERALL® for both d- and l-amphetamine.

Example 5

Controlled Release Capsules (SPD465 25 mg/capsule)

A controlled release capsule was produced by combining the immediate release pellets of Example 1, and delayed release pellets of Example 3 and Example 4. The theoretical milligram/capsule of components for controlled release capsules, 25 mg/capsule are listed in Table 5. The theoretical potency of each pellet type was derived based on the starting ingredients for manufacture. Based on the actual manufacturing process, along with observation of process losses, the target potency value was: 170 mg/gram for Example 1 immediate release pellets, 107.1 mg/gram for Example 3 delayed release pellets, and 100.2 mg/gram for Example 4 delayed release pellets. The components are listed by theoretical milligrams/capsule in Table 6.

TABLE 6

| Components | Theoretical milligram/capsule |
|---|---|
| Immediate release pellets of Example 1* | 43.86 |
| Delayed release pellets of Example 3** | 69.62 |
| Delayed release pellets of Example 4*** | 74.40 |
| Capsule shell | 61.00 |
| Total | 248.88 |

Figure 5:
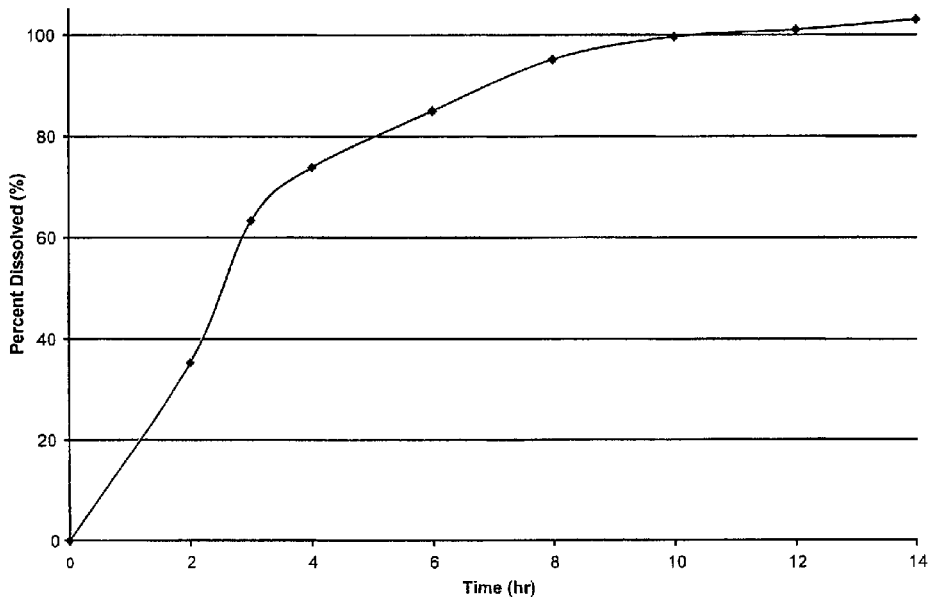
FIG. 5 is a graph showing the dissolution profile of a 25 mg mixed amphetamine salt 3-bead composition according to the invention. The following pH conditions were used: at 0-2 hours, pH 1.1; at 2-3 hours, pH 6.0; at three hours and greater, pH 7.5.

*The theoretical fill weight was calculated based on the theoretical potency of Example 1 immediate release pellets, 190 mg/gram.
**The theoretical fill weight was calculated based on the theoretical potency of Example 3 delayed release pellets, 119.7 mg/gram.
***The theoretical fill weight was calculated based on the theoretical potency of Example 4 delayed release pellets, 112.0 mg/gram.
The dissolution profile for SPD465 25 mg (lot no. A03547A) is shown in FIG. 5.

Example 6

Controlled Release Capsules (SPD465 37.5 mg/capsule)

A controlled release capsule was produced by combining the immediate release pellets of Example 1, and the delayed release pellets of Example 3 and Example 4. The theoretical milligram/capsule of components for controlled release capsules, 37.5 mg/capsule are listed in Table 7. The theoretical potency of each pellet type was derived based on the starting ingredients for manufacture. Based on the actual manufacturing process, along with observation of process losses, the target potency value was: 170 mg/gram for Example 1 immediate release pellets, 107.1 mg/gram for Example 3 delayed release pellets, and 100.2 mg/gram for Example 4 delayed release pellets. The components are listed by theoretical milligrams/capsule in Table 7.

TABLE 7

| Components | Theoretical milligram/capsule |
|---|---|
| Immediate release pellets of Example 1* | 65.79 |
| Delayed release pellets of Example 3** | 104.43 |
| Delayed release pellets of Example 4*** | 111.6 |
| Capsule shell | 81.00 |
| Total | 362.82 |

Figure 6:
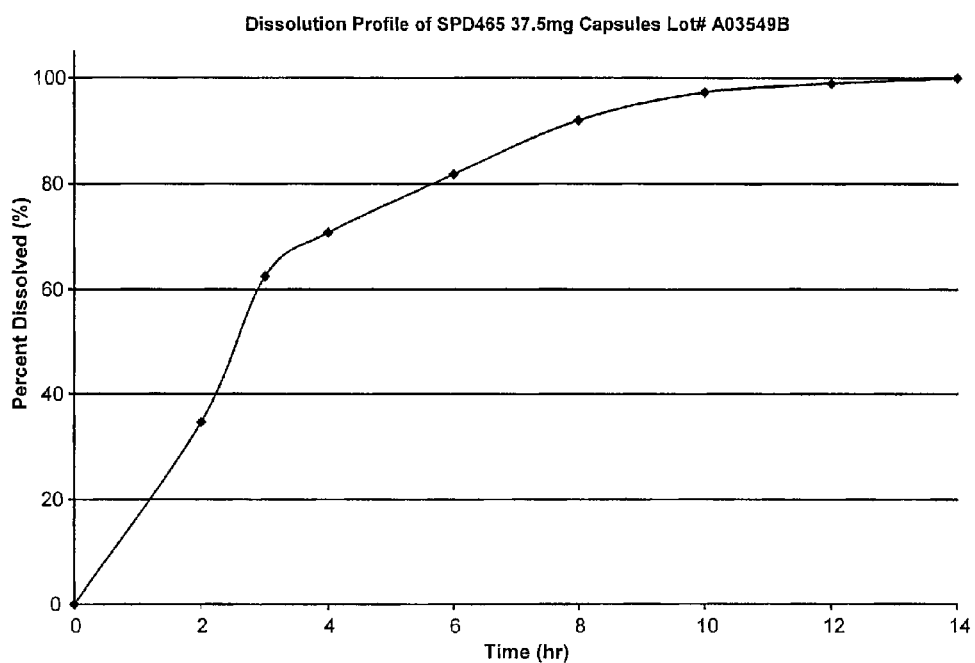
FIG. 6 is a graph showing the dissolution profile of a 37.5 mg mixed amphetamine salt 3-bead composition according to the invention. The following pH conditions were used: at 0-2 hours, pH 1.1; at 2-3 hours, pH 6.0; at three hours and greater, pH 7.5.

*The theoretical fill weight was calculated based on the theoretical potency of Example 1 immediate release pellets, 190 mg/gram.
**The theoretical fill weight was calculated based on the theoretical potency of Example 3 delayed release pellets, 119.7 mg/gram.
***The theoretical fill weight was calculated based on the theoretical potency of Example 4 delayed release pellets, 112.0 mg/gram.
The dissolution profile for SPD465 37.5 mg (lot no. A03549B) is shown in FIG. 6.

Example 7

Controlled Release Capsules (SPD465 50 mg/capsule)

A controlled release capsule was produced by combining the immediate release pellets of Example 1, and delayed release pellets of Example 3 and Example 4. The theoretical milligram/capsule of components for controlled release capsules, 50 mg/capsule are listed in Table 8. The theoretical potency of each pellet type was derived based on the starting ingredients for manufacture. Based on the actual manufacturing process, along with observation of process losses, the target potency value was: 170 mg/gram for Example 1 immediate release pellets, 107.1 mg/gram for Example 3 delayed release pellets, and 100.2 mg/gram for Example 4 delayed release pellets. The components are listed by theoretical milligrams/capsule in Table 8.

TABLE 8

| Components | Theoretical milligram/capsule |
|---|---|
| Immediate release pellets of Example 1* | 87.72 |
| Delayed release pellets of Example 3** | 139.24 |
| Delayed release pellets of Example 4*** | 148.80 |
| Capsule shell | 96.00 |
| Total | 471.76 |

Figure 7:
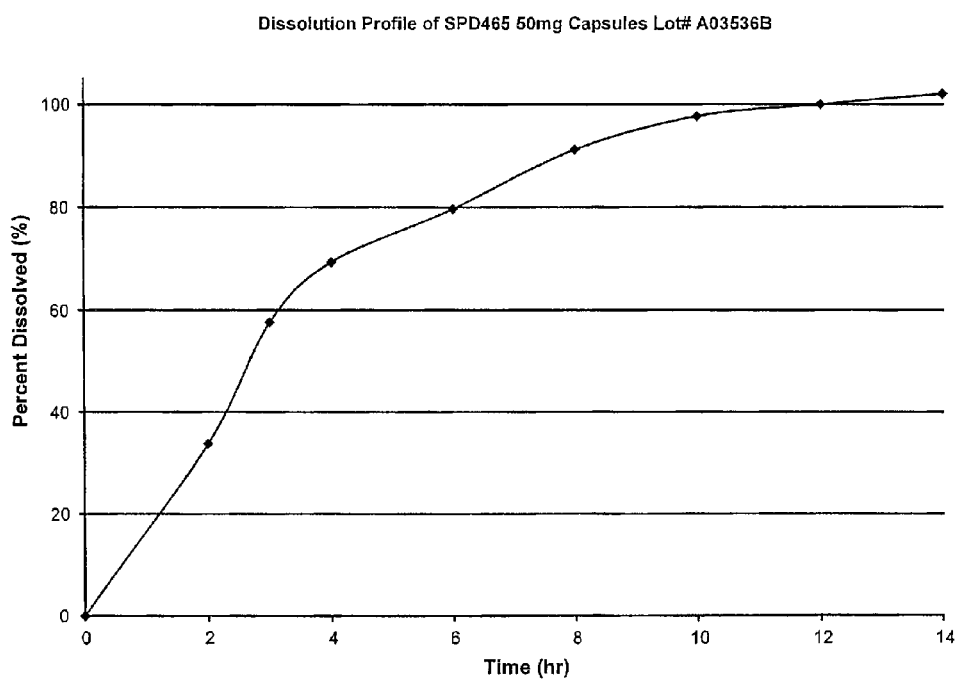
FIG. 7 is a graph showing the dissolution profile of a 50 mg mixed amphetamine salt 3-bead composition according to the invention. The following pH conditions were used: at 0-2 hours, pH 1.1; at 2-3 hours, pH 6.0; at three hours and greater, pH 7.5.

*The theoretical fill weight was calculated based on the theoretical potency of Example 1 immediate release pellets, 190 mg/gram.
**The theoretical fill weight was calculated based on the theoretical potency of Example 3 delayed release pellets, 119.7 mg/gram.
***The theoretical fill weight was calculated based on the theoretical potency of Example 4 delayed release pellets, 112.0 mg/gram.
The dissolution profile for SPD465 50 mg (lot no. A03536B) is shown in FIG. 7.

Example 8

A Phase I Pharmacokinetic Study in Healthy Adult Volunteers to Evaluate the Pharmacokinetic Profile of the 37.5 mg Controlled Release Composition of Example 6 Relative to 25 mg ADDERALL XR®+12.5 mg Mixed Amphetamine Salts IR (Clinical Study 103)

The objective of this study was to assess the pharmacokinetics (PK) of the 37.5 mg controlled release composition of Example 6 compared to a reference treatment of ADDERALL XR® 25 mg followed by a 12.5 mg dose of the mixed amphetamine salts immediate-release (IR) formulation disclosed in Example 1 administered 8 hours later.

This was an open-label, randomized, single-dose, 2-way crossover, 2-period, phase I study with at least a 7-day washout between each period. In period 1, subjects were randomized to receive a single morning dose of one of the two study formulations. Each subject was crossed over to receive the alternate treatment in the subsequent period. In Treatment A, subjects received a single 37.5 mg dose of the controlled release composition of Example 6. In Treatment B, subjects received a single 25 mg dose of ADDERALL XR® followed by a 12.5 mg dose of the mixed amphetamine salts immediate release formulation of Example 1 administered 8 hours later. See Table 9.

TABLE 9

| Treatment | Composition | Dose | Route of Administration |
|---|---|---|---|
| A | Composition of Example 6 (Batch no. A03383-002L) | 1 × 37.5 mg | Oral |
| B | ADDERALL XR ® and the immediate release bead of Example 1 | 1 × 25 mg ADDERALL XR ® (Batch no. A02936B) followed 8 hours later by 1 × 12.5 mg bead of Example 1 (Batch no. A03383-003L) | Oral |

At screening, each subject provided a medical and medication history. A 12-lead electrocardiogram (ECG), vital signs, height, and weight were obtained. Blood and urine samples were collected for routine clinical laboratory analysis, antibody screening for Human Immunodeficiency Virus (HIV), Hepatitis B and C, and urine alcohol and drug screen. A serum pregnancy test was conducted on all women of child-bearing potential (WOCP) during screening.

For each treatment period, subjects reported to the clinic the morning prior to dosing at which time continued eligibility was confirmed by urine alcohol and drug screen, urine pregnancy test for WOCP, weight, routine clinical laboratory analysis, 12-lead ECGs, and vital signs. Subjects also underwent a physical examination, and a brief medical and medication history was completed.

Blood samples for the determination of plasma d- and l-amphetamine concentrations were collected at specified times in each treatment period. Vital sign measurements were obtained prior to dosing and at 2, 4, 8, 12, 24, and 60 hours post-dose. Adverse events (AEs) and concomitant medications were reported throughout each treatment period. Twelve-lead ECG measurements were collected prior to dosing and at 2, 4, 8, 12, 24, and 60 hours post-dose.

Exit assessments at the end of each treatment period included a physical examination, 12-lead ECG, routine clinical laboratory measurements, vital signs, and AE assessment. A serum pregnancy test for WOCP was performed at study exit/withdrawal. A follow-up telephone call to assess AEs was made to all subjects 30±2 days after last exposure to study medication.

Duration of study: 11 days (two treatment periods, each with four days of confinement and a 7-day washout period between study medication dosing).

Pharmacokinetics: d- and l-amphetamine concentrations were determined in plasma samples collected at the following times: 30 minutes prior to dosing (Time 0) on Day 1, and at 1, 2, 3, 4, 5, 6, 7, 8, 9, 10, 12, 14, 16, 24, 36, 48, and 60 hours post-dose for each treatment. Plasma d- and l-amphetamine concentrations were measured with a validated liquid chromatography with tandem mass spectrometry (LC/MS/MS) method.

Statistical Methods:

Pharmacokinetic parameters were compared between treatment groups using an analysis of variance (ANOVA) with sequence, period, and treatment as fixed effects, and subject nested within sequence as a random effect. This analysis was performed for the natural log transformations of maximum plasma concentration ($C_{max}$), area under the plasma concentration-time curve from time 0 to time infinity ($AUC_{(0-inf)}$), and area under the plasma concentration-time curve from time 0 to last measured time ($AUC_{(0-last)}$) using SAS PROC MIXED.

For $C_{max}$, $AUC_{(0-inf)}$, and $AUC_{(0-last)}$, exponentiated least squares (LS) means for each treatment were obtained by taking the antilog of the LS means on the log scale. Ratios of the exponentiated LS means for the test treatment (SPD465 37.5 mg) relative to the reference treatment (25 mg ADDERALL XR® followed by 12.5 mg mixed amphetamine salts IR 8 hours later) and 90% confidence intervals (CIs) of the ratios were provided. The 90% CIs were obtained by taking the antilog of the 90% CIs for the difference between the LS means on the log scale.

$C_{max}$, $AUC_{(0-last)}$, $AUC_{(0-inf)}$, terminal half-life (t½), terminal phase rate constant ($\lambda_Z$), and time of maximum plasma concentration ($t_{max}$) were summarized descriptively for each treatment.

Adverse events were coded using the Medical Dictionary for Regulatory Activities (MedDRA) version 7.1 adverse event dictionary. The frequency of treatment-emergent adverse events (TEAE) was tabulated by body system and preferred term for each treatment. AEs were further summarized by severity, relationship to study drug, gender, and ethnicity. AEs leading to study withdrawal were summarized separately by body system, preferred term, and treatment group.

Clinical laboratory evaluations were summarized by treatment and visit. Hematology and biochemistry were summarized using descriptive statistics; discrete urinalysis measurements were summarized using frequencies and percents and continuous urinalysis measurements were summarized using descriptive statistics. Laboratory data outside the normal range was flagged in the subject data listings.

Vital signs, including pulse, systolic and diastolic BP, and respiration rate, were summarized by treatment for each measured time point using descriptive statistics. Change from baseline was also calculated and summarized for each post baseline time point.

Results:

Subject demographics: The overall gender distribution was 60% (12/20) females and 40% (8/20) males. The overall racial distribution was 90% (18/20) White and 10% (2/20) Black/African-American. The age of the study subjects ranged from 21-50 years with an overall mean age (SD) of 30.0 years (8.83). Subjects weighed between 61 kg and 97 kg with a mean weight (SD) of 73.8 kg (10.15), and height ranged between 158 cm-188 cm with a mean height (SD) of 172.6 cm (8.05). Body Mass Index ranged between 20.1 kg/m$^2$-29.2 kg/m$^2$ with a mean BMI (SD) of 24.75 (2.267).

Figure 9:
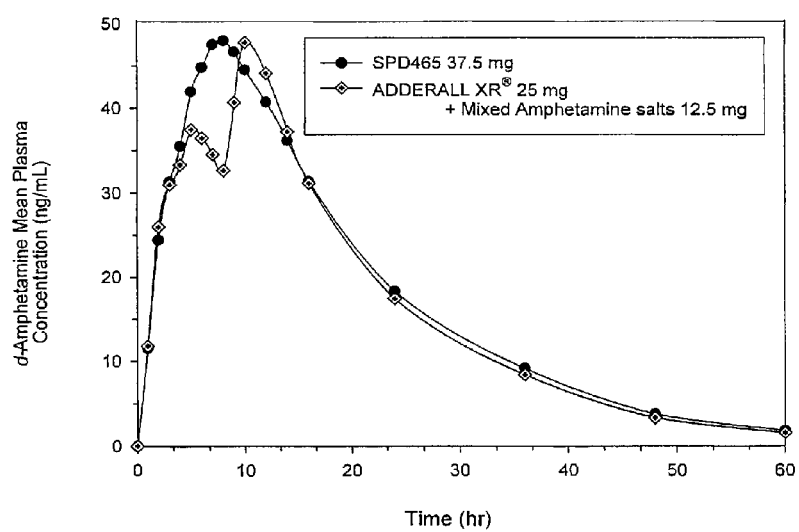
FIG. 9 graphically illustrates the mean d-amphetamine plasma concentration of SPD465 37.5 mg compared to ADDERALL XR® 25 mg followed by immediate release mixed amphetamine salts 12.5 mg 8 hours later.

Pharmacokinetic Results:

FIG. 9 shows the d-amphetamine plasma concentration profile of SPD465 37.5 mg compared to ADDERALL XR® (25 mg) followed by immediate release mixed amphetamine salts (12.5 mg) eight hours later. Exposure to d-amphetamine, as described by $C_{max}$ and AUC values, was comparable following Treatment A and Treatment B. The 90% CI of the test-to-reference ratios were within the bioequivalence range of 80%-125%.

Figure 10:
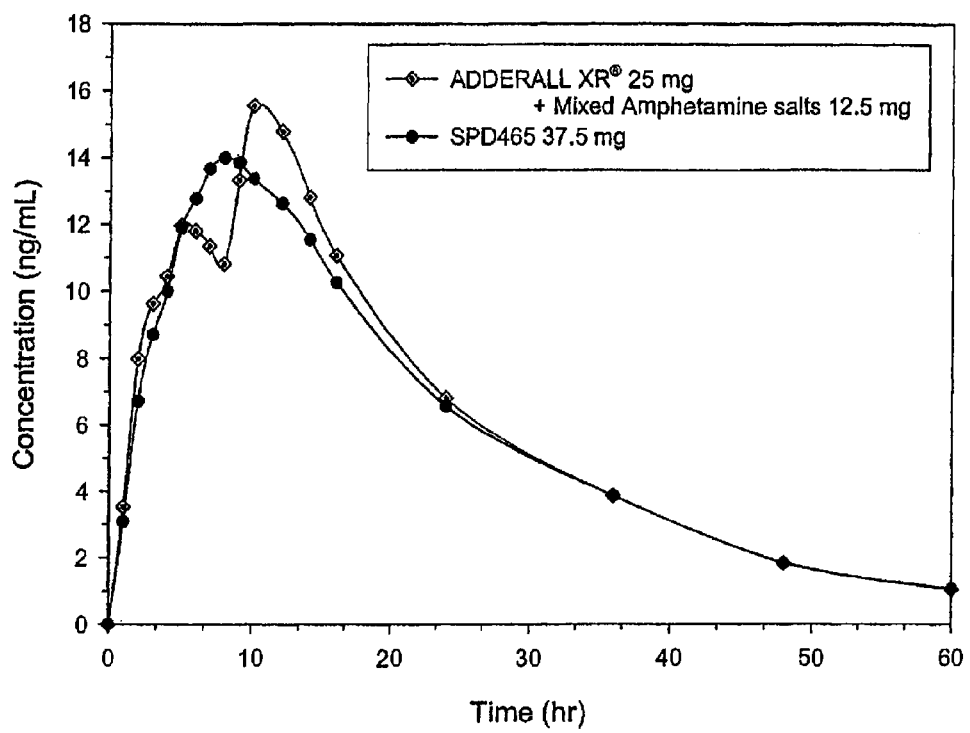
FIG. 10 graphically illustrates the mean l-amphetamine plasma concentration of SPD465 37.5 mg compared to ADDERALL XR® 25 mg followed by immediate release mixed amphetamine salts 12.5 mg 8 hours later.
Figure 11:
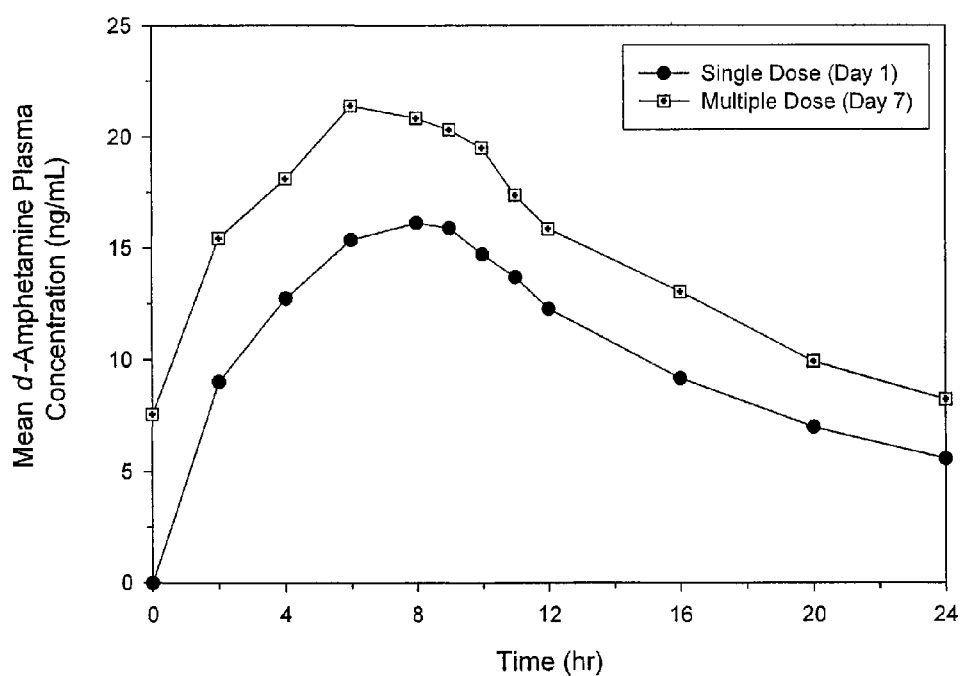
FIG. 11 graphically illustrates mean d-amphetamine plasma concentrations over time following administration of a single dose and seven once-daily doses of 12.5 mg SPD465 to healthy subjects.
Figure 12:
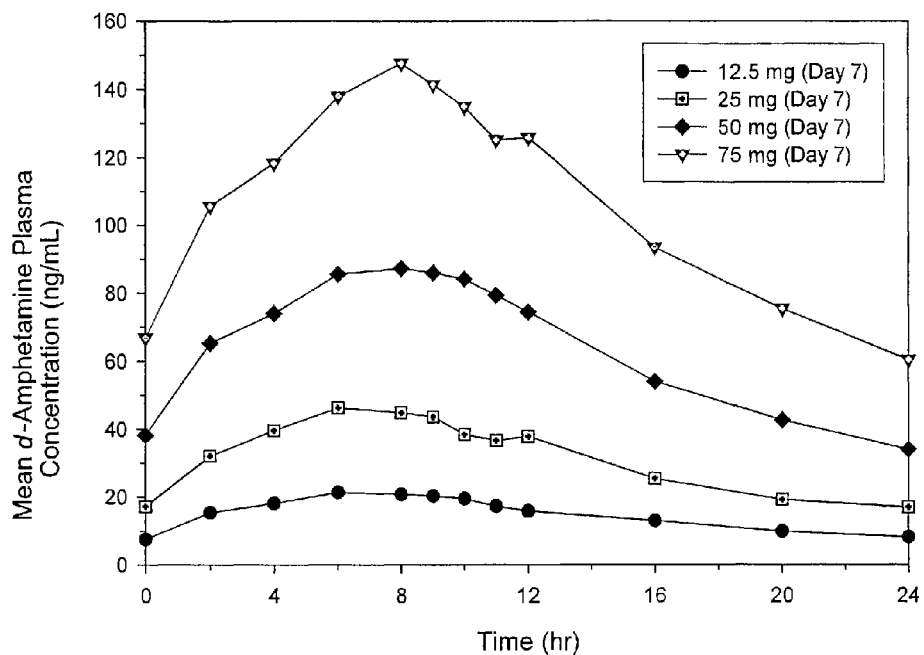
FIG. 12 graphically illustrates mean d-amphetamine plasma concentrations over time following administration of seven once-daily doses of SPD465 to healthy subjects.
Figure 13:
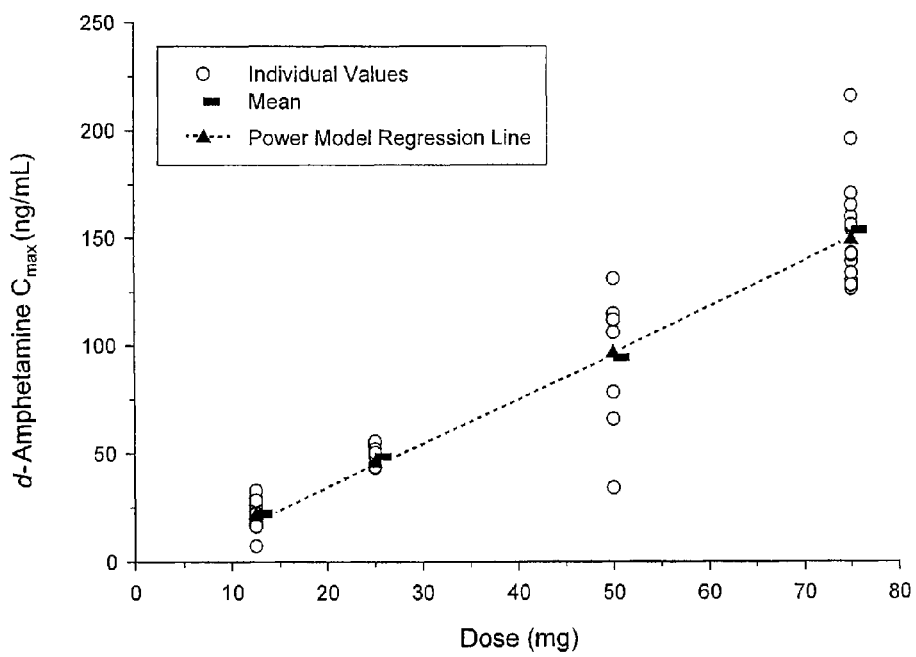
FIG. 13 graphically illustrates the power model analysis of mean and individual Day 7 Cmax values for d-amphetamine by dose.
Figure 14:
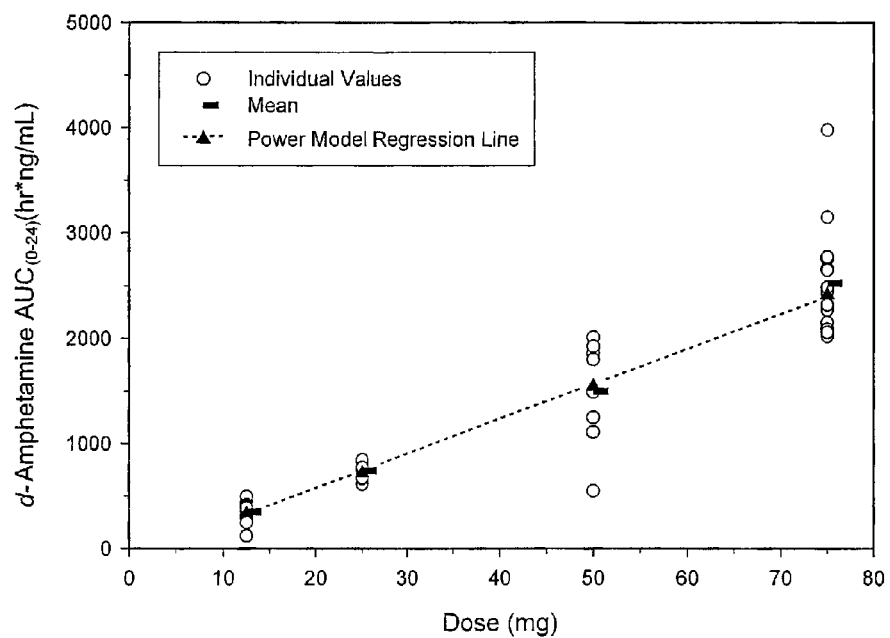
FIG. 14 graphically illustrates the power model analysis of mean and individual Day 7 $AUC_{0-24}$ values for d-amphetamine by dose.
Figure 15:
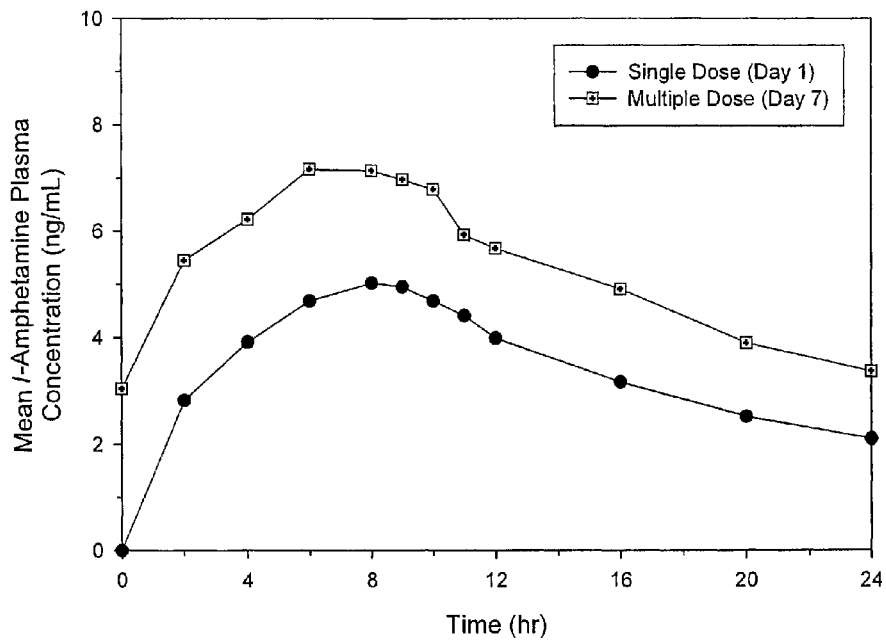
FIG. 15 graphically illustrates mean l-amphetamine plasma concentrations over time following administration of a single dose and seven once-daily doses of 12.5 mg SPD465 to healthy subjects.
Figure 16:
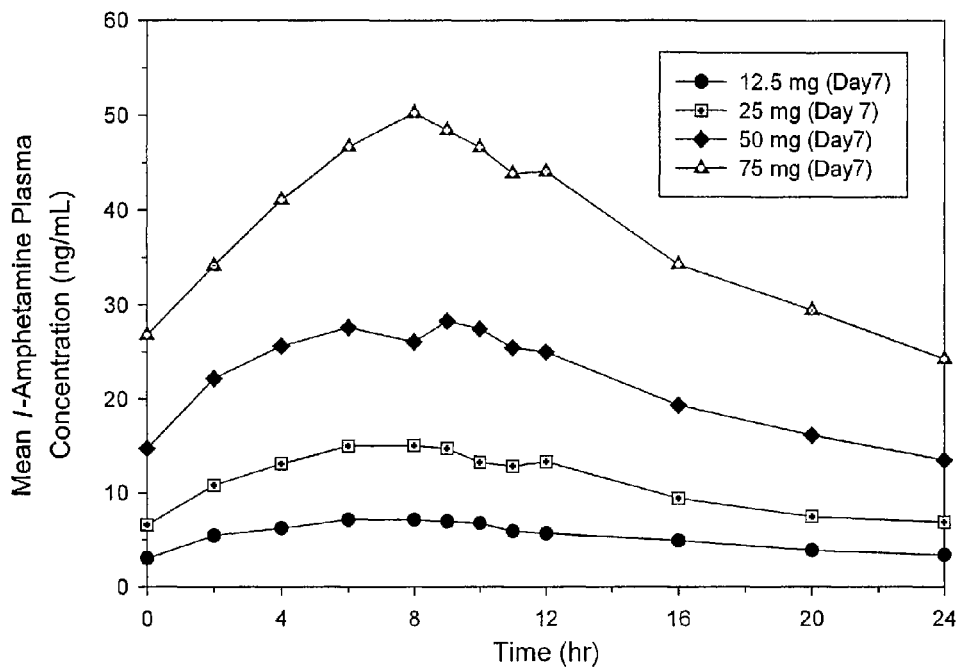
FIG. 16 graphically illustrates mean d-amphetamine plasma concentrations over time following administration of seven once-daily doses of SPD465 to healthy subjects.
Figure 17:
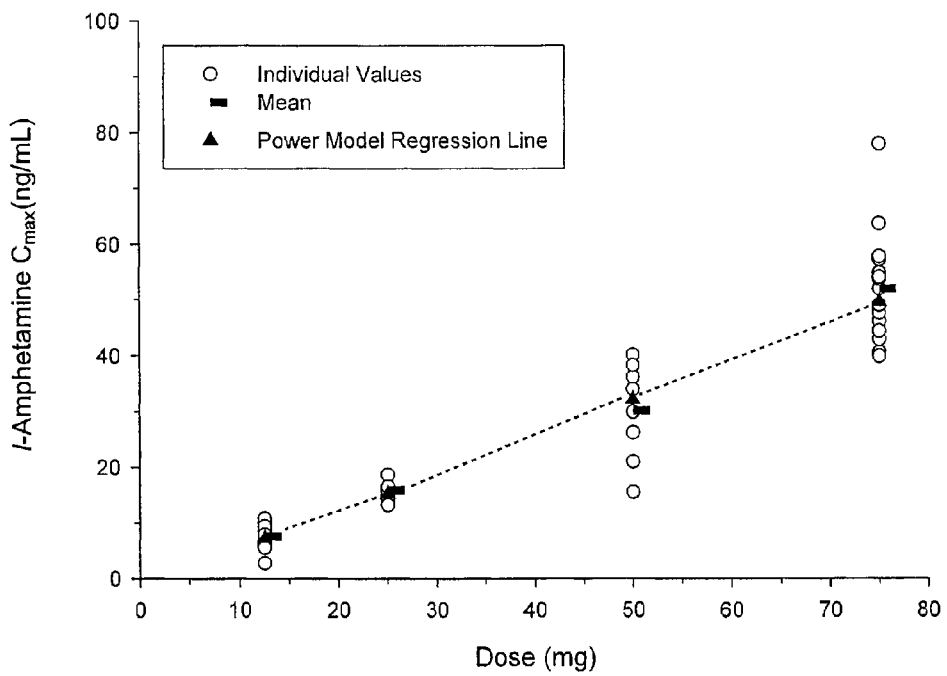
FIG. 17 graphically illustrates the power model analysis of mean and individual Day 7 Cmax values for l-amphetamine by dose.
Figure 18:
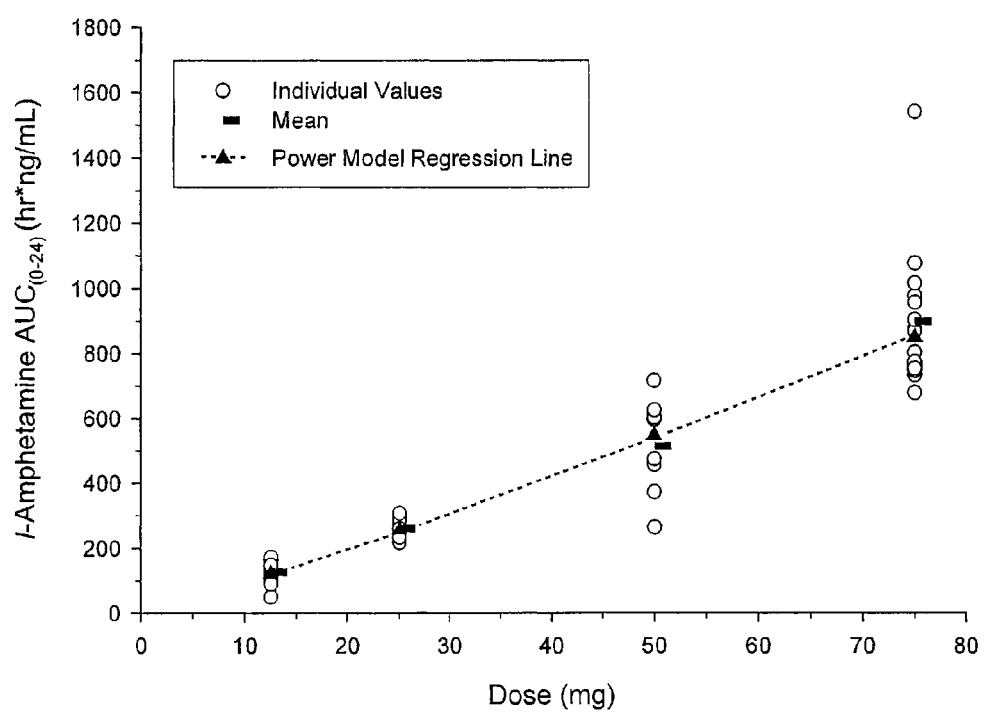
FIG. 18 graphically illustrates the power model analysis of mean and individual Day 7 $AUC_{0-24}$ values for l-amphetamine by dose.

FIG. 10 shows the l-amphetamine plasma concentration profile of SPD465 37.5 mg compared to ADDERALL XR® (25 mg) followed by immediate release mixed amphetamine salts (12.5 mg) eight hours later. $C_{max}$ and AUC values of l-amphetamine following a dose of Treatment A were similar to those following Treatment B; 90% CI of the test-to-reference ratios were within the bioequivalence range of 80%-125%.

The elimination half lives of d- and l-amphetamine were similar for both treatments. See Table 10.

Conclusions:

Treatment A and Treatment B were bioequivalent with respect to $C_{max}$ and AUC of d- and l-amphetamine. All treatments were well tolerated and all reported AEs were expected.

Example 9

A Phase I Study to Evaluate the Pharmacokinetic Profile of SPD 465 50 mg Under Fed, Fasted, and Sprinkled Conditions in Healthy Adult Volunteers (Clinical Study 105)

This was an open-label, randomized, single-dose, 3-way crossover, 3-period study with a minimum 7-day washout between each study drug dosing. Sixteen healthy male and female subjects between the ages of 18 and 55 participated in the study. This study was designed to evaluate (1) the effect of a high fat meal on the PK of SPD465 50 mg compared to a reference treatment and (2) the effect of a SPD465 50 mg capsule sprinkled on applesauce compared to a reference treatment. The reference treatment was a 50 mg dose of SPD465 following an at least 10-hour fast. See Table 11. The primary objective of this study was to assess the effect of a high fat meal on the bioavailability of SPD465 relative to the fasted state.

TABLE 10

Plasma Pharmacokinetic Parameters for d- and l-Amphetamine After a Single Dose of 37.5 mg SPD465 (Treatment A) or 25 mg ADDERALL XR ® + 12.5 mg Mixed Amphetamine Salts (Treatment B)

| Parameters | Treatment A | | | Treatment B | | | Exponentiated LS Mean | |
|---|---|---|---|---|---|---|---|---|
| | n | Mean (±SD) | LS Mean | n | Mean (±SD) | LS Mean | Ratio % (A)/(B) | 90% CI |
| d-Amphetamine | | | | | | | | |
| $C_{max}$ (ng/mL) | 20 | 50.3 (7.5) | 49.7 | 19 | 49.3 (7.4) | 49.2 | 101.0 | (96.9, 105.3) |
| $AUC_{(0-last)}$ (ng · hr/mL) | 20 | 1058.0 (184.5) | 1042.4 | 19 | 997.9 (172.9) | 1000.8 | 104.2 | (100.2, 108.3) |
| $AUC_{(0-inf)}$ (ng · hr/mL) | 20 | 1084.9 (196.2) | 1067.8 | 19 | 1019.5 (181.3) | 1022.5 | 104.4 | (100.3, 108.7) |
| $T_{max}$ (hr) | 20 | 8.2 (2.0) | | 19 | 9.7(2.1) | | | |
| l-Amphetamine | | | | | | | | |
| $C_{max}$ (ng/mL) | 20 | 14.7 (2.2) | 14.6 | 19 | 16.0 (2.3) | 16.0 | 90.9 | (87.5, 94.4) |
| $AUC_{(0-last)}$ (ng · hr/mL) | 20 | 353.5 (66.0) | 347.6 | 19 | 364.1 (66.5) | 364.6 | 95.3 | (91.0, 99.8) |
| $AUC_{(0-inf)}$ (ng · hr/mL) | 20 | 372.8 (73.5) | 365.9 | 19 | 382.3 (69.0) | 383.9 | 95.3 | (91.2, 99.6) |
| $T_{max}$ (hr) | 20 | 8.4 (2.1) | | 19 | 10.7 (1.3) | | | |

LS = Least squares

TABLE 11

| Treatment | Study Drug | Dosage |
|---|---|---|
| Treatment A (reference) | SPD465 (batch no. A03445-001L) | 1 × 50 mg capsule after an at least 10 hour fast |
| Treatment B | SPD465 (batch no. A03445-001L) | 1 × 50 mg capsule following a high fat meal |
| Treatment C | SPD465 (batch no. A03445-001L) | 1 × 50 mg capsule sprinkled on 1 tablespoon of applesauce |

The study included three single-dose treatment periods separated by a minimum 7-day washout period between study drug dosing. On study day 1 of each period, according to the randomization schedule, the subjects were administered a single dose of SPD465 50 mg following an at least 10-hour fast, SPD465 50 mg following a standard high fat meal or the contents of a SPD465 50 mg capsule sprinkled on applesauce.

Blood samples for the determination of plasma d- and l-amphetamine concentrations were collected 30 minutes prior to drug administration (0 hour) and at 1, 2, 3, 4, 5, 6, 7, 8, 9, 10, 12, 14, 16, 24, 36, 48, and 60 hours after dosing in each treatment period.

Results:

d-amphetamine d-Amphetamine plasma levels as described by $C_{max}$, $AUC_{(0-last)}$, and $AUC_{(0-inf)}$ were highest in fasted subjects, slightly lower in subjects receiving SPD465 sprinkled on applesauce, and lowest in subjects pretreated with a high-fat meal. See Tables 12 and 13. The 90% CI of the test-to-reference ratios, with fasted as the reference treatment, were within the typically acceptable bioequivalence range of 80% to 125%, which indicates that the there were no significant differences across the unfed/fed conditions. The CIs on the ratios between subjects receiving the high-fat meal and fasted subjects were less than 100%.

The median time to maximum d-amphetamine plasma concentrations ($T_{max}$) in fasted subjects and those who received SPD465 sprinkled on applesauce was 7 and 7.5 hours, respectively. The $T_{max}$ in subjects who received SPD465 following a high-fat meal was delayed approximately 4 to 5 hours with a median value of 12 hours.

TABLE 12 d-Amphetamine Plasma Pharmacokinetic Parameters Following a Single Dose Administration of 50 mg SPD465

| Parameter | Fasted (A) n = 14 | High Fat Meal (B) n = 16 | Sprinkled (C) n = 16 |
|---|---|---|---|
| $C_{max}$ (ng/ml) | 72.3 | 60.0 | 67.3 |
| Mean (SD) | (13.72) | (7.09) | (7.69) |
| $T_{max}$ (hr) | 7.0 | 12.0 | 7.5 |
| Median (Min, Max) | (6.0, 10.0) | (8.0, 14.0) | (5.0, 9.0) |
| $AUC_{(0-last)}$ (hr * ng/ml) | 1531.9 | 1382.6 | 1450.8 |
| Mean (SD) | (292.36) | (289.85) | (253.28) |
| $AUC_{(0-inf)}$ (hr * ng/ml) | 1589.5 | 1433.8 | 1497.9 |
| Mean (SD) | (359.98) | (339.50) | (300.83) |
| λz (1/hr) | 0.07 | 0.07 | 0.07 |
| Mean (SD) | (0.014) | (0.011) | (0.012) |
| $t_{1/2}$ (hr) | 10.9 | 10.5 | 10.6 |
| Mean (SD) | (2.60) | (2.11) | (2.22) |

TABLE 13

Statistical Analysis Results of Plasma d-Amphetamine Following a Single Dose Administration of 50 mg SPD465

| | Exponentiated LS Means | | | Ratio of LS Means | | 90% CI | |
|---|---|---|---|---|---|---|---|
| Parameter | Fasted (A) n = 14 | High-Fat Meal (B) n = 16 | Sprinkled (C) n = 16 | B/A | C/A | B/A | C/A |
| $AUC_{(0-inf)}$ (hr * ng/mL) | 1528.3 | 1392.5 | 1463.7 | 91.1 | 95.8 | 86.7, 95.8 | 91.1, 100.6 |
| $AUC_{(0-last)}$ (hr * ng/mL) | 1484.2 | 1350.3 | 1424.5 | 91.0 | 96.0 | 86.7, 95.5 | 91.5, 100.7 |
| $C_{max}$ (ng/mL) | 69.6 | 59.4 | 66.7 | 85.3 | 95.8 | 80.4, 90.5 | 90.3, 101.6 |

LS = Least squares l-amphetamine l-Amphetamine plasma levels as described by $C_{max}$, $AUC_{(0-last)}$, and $AUC_{(0-inf)}$ were highest in fasted subjects, slightly lower in subjects receiving SPD465 sprinkled on apple sauce, and lowest in subjects pretreated with a high-fat meal. See Tables 14 and 15. The 90% CI of the test-to-reference ratios, with fasted as the reference treatment, were within the typically acceptable bioequivalence range of 80% to 125%, which indicates that the there were no significant differences across the unfed/fed conditions. The CIs on the ratios between subjects receiving the high-fat meal and fasted subjects were less than 100%.

The median time to maximum l-amphetamine plasma concentrations ($T_{max}$) in fasted subjects and those who received SPD465 sprinkled on applesauce was 7.5 and 8 hours, respectively. The $T_{max}$ in subjects who received SPD465 following a high-fat meal was delayed approximately 4.5 hours with a median value of 12 hours.

TABLE 14 l-Amphetamine Plasma Pharmacokinetic Parameters Following a Single Dose Administration of 50 mg SPD465

| Parameter | Fasted (A) n = 14 | High Fat Meal (B) n = 16 | Sprinkled (C) n = 16 |
|---|---|---|---|
| $C_{max}$ (ng/ml) | 21.1 | 17.6 | 20.0 |
| Mean (SD) | (3.74) | (2.21) | (2.50) |
| $T_{max}$ (hr) | 7.5 | 12.0 | 8.0 |
| Median (Min, Max) | (6.0, 12.0) | (8.0, 14.0) | (5.0, 12.0) |
| $AUC_{(0-last)}$ (hr * ng/ml) | 506.9 | 448.3 | 479.2 |
| Mean (SD) | (107.92) | (107.79) | (100.83) |
| $AUC_{(0-inf)}$ (hr * ng/ml) | 545.2 | 481.7 | 511.4 |
| Mean (SD) | (147.92) | (138.43) | (127.13) |
| λz (1/hr) | 0.05 | 0.06 | 0.06 |
| Mean (SD) | (0.014) | (0.013) | (0.011) |
| $t_{1/2}$ (hr) | 13.6 | 12.8 | 13.0 |
| Mean (SD) | (3.70) | (3.30) | (3.22) |

TABLE 15

Statistical Analysis Results of Plasma l-Amphetamine Following a Single Dose Administration of 50 mg SPD465

| | Exponentiated LS Means | | | | | |
|---|---|---|---|---|---|---|
| | Fasted (A) | High-Fat Meal (B) | Sprinkled (C) | Ratio of LS Means | 90% CI | |
| Parameter | n = 14 | n = 16 | n = 16 | B/A  C/A | B/A | C/A |
| $AUC_{(0-inf)}$ (hr * ng/mL) | 522.3 | 463.4 | 495.0 | 88.7  94.8 | 83.9, 93.9 | 89.6, 100.3 |
| $AUC_{(0-last)}$ (hr * ng/mL) | 492.2 | 436.1 | 468.1 | 88.6  95.1 | 83.8, 93.7 | 90.0, 100.5 |
| $C_{max}$ (ng/mL) | 20.4 | 17.4 | 19.8 | 85.2  96.9 | 80.2, 90.6 | 91.2, 103.0 |

LS = Least squares

Conclusion

There were no statistically significant differences in plasma d- or l-amphetamine levels when SPD465 50 mg was administered to subjects in a fasted state, following a high-fat meal, or when the SPD465 was administered with applesauce. The pharmacokinetic findings indicate that in the presence of a high-fat meal, the rate of absorption of d- and l-amphetamines is decreased but the extent of absorption is unaffected. Thus, these results show that SPD465 administered with food was bioequivalent to SPD465 administered without food.

Example 10

An Open-Label, Incomplete Block Randomization, Three-Period, Four Treatment, Dose Escalating Study of the Pharmacokinetics of SPD 465 Administered at Steady State in Healthy Adult Volunteers (Clinical Study 110)

The primary objective of this study was to determine the pharmacokinetics of SPD465 following repeat dose administration over a range of doses from 12.5 mg to 75 mg. All 18 subjects received SPD465 at a dose of 12.5 mg once daily for 7 days in Period 1. The dose was increased so that about half the subjects received 25 mg and the others received 50 mg once daily for the next 7 days (Period 2). In Period 3, all subjects were increased to 75 mg once daily for 7 days following Period 2.

Blood samples were collected from each subject on days 1, 5, 6 and 7 of each Period for the determination of d- and l-amphetamine concentrations. Blood and urine samples were collected on day 7 of Period 3 for metabolite identification.

Subjects were administered the SPD465 dosages described in Table 16.

TABLE 16

| Dose level | Mode of administration | Batch Number |
|---|---|---|
| 12.5 mg (Period 1) | 1 × 12.5 mg capsule | A08763A |
| 25 mg (Period 2) | 1 × 25 mg capsule | A08767A |
| 50 mg (Period 2) | 1 × 50 mg capsule | A08762A |
| 75 mg (Period 3) | 2 × 37.5 mg capsules | A08761A |

The calculated pharmacokinetic parameters included:

| | |
|---|---|
| Cmax: | maximum plasma concentration |
| Tmax: | time of maximum plasma concentration |
| $AUC_{0-24}$: | area under the plasma concentration-time curve from time 0 to time 24 hours |
| Cmin: | minimum plasma concentration |
| CL/F: | apparent oral clearance |
| CL/F/Wt: | weight adjusted apparent oral clearance |
| R: | accumulation ratio |
| $AUC_{0-24}/AUC_{0-24}$ 12.5 mg: | area under the plasma concentration-time curve from time 0 to time 24 hours on Day 7 at 25 mg, 50 mg, and 75 mg relative to the $AUC_{0-24}$ on Day 7 at 12.5 mg. |

Pharmacokinetic parameters were calculated by non-compartmental techniques using WinNonlin® Professional version 4.1. All calculations were based on actual sampling times. The pharmacokinetic parameters were determined from plasma concentration-time data measured using a validated liquid chromatography with tandem mass spectrometry (LC/MS/MS) method.

The pharmacokinetic results are graphically illustrated in FIGS. 11-12 and 15-16 shown in Table 17.

TABLE 17

| | | Single dose (Day 1) | Multiple dose (Day 7) | | | |
|---|---|---|---|---|---|---|
| Parameter | Statistic | 12.5 mg (N = 18)* | 12.5 mg (N = 18)* | 25 mg (N = 9) | 50 mg (N = 8) | 75 mg (N = 17)* |
| | | d-amphetamine | | | | |
| Cmax (ng/mL) | Mean (SD) | 17.0 (2.9) | 22.4 (5.8) | 48.5 (4.6) | 94.2 (32.1) | 153.5 (24.6) |
| Tmax (hr) | Median (min., max.) | 8.0 (6.0, 9.0) | 6.0 (2.0, 10.1) | 8.0 (6.0, 9.0) | 6.0 (4.0, 12.1) | 8.0 (6.0, 12.0) |
| $AUC_{0-24}$ (hr * ng/mL) | Mean (SD) | 248.5 (45.3) | 351.3 (87.5) | 742.0 (77.5) | 1499.7 (504.9) | 2526.2 (495.1) |
| Cmin (ng/mL) | Mean (SD) | — | 7.6 (2.9) | 17.2 (5.6) | 38.2 (10.5) | 66.8 (23.8) |
| CL/F (L/hr) | Mean (SD) | 39.0 (7.2) | 29.5 (13.5) | 25.5 (2.8) | 29.5 (16.6) | 22.9 (3.7) |
| CL/F/Wt (L/hr/kg) | Mean (SD) | 0.51 (0.09) | 0.40 (0.18) | 0.35 (0.05) | 0.40 (0.23) | 0.31 (0.06) |
| R | Mean (SD) | — | 1.4 (0.30) | — | — | — |

TABLE 17-continued

| Parameter | Statistic | Single dose (Day 1) 12.5 mg (N = 18)* | Multiple dose (Day 7) | | | |
|---|---|---|---|---|---|---|
| | | | 12.5 mg (N = 18)* | 25 mg (N = 9) | 50 mg (N = 8) | 75 mg (N = 17)* |
| $AUC_{0-24}/$ | Mean | — | — | 2.2 | 4.2 | 8.0 |
| $AUC_{0-24}$ 12.5 mg | (SD) | | | (0.4) | (0.6) | (4.0) |
| | | l-amphetamine | | | | |
| Cmax | Mean | 5.2 | 7.6 | 15.9 | 30.2 | 52.0 |
| (ng/ml) | (SD) | (0.9) | (1.8) | (1.6) | (8.7) | (9.6) |
| Tmax | Median | 8.0 | 8.0 | 8.0 | 9.0 | 8.0 |
| (hr) | (min., max.) | (6.0, 10.0) | (2.0, 10.1) | (4.0, 9.0) | (4.0, 12.1) | (6.0, 12.0) |
| $AUC_{0-24}$ | Mean | 81.3 | 126.4 | 261.5 | 514.7 | 899.3 |
| (hr * ng/mL) | (SD) | (14.8) | (29.9) | (31.8) | (148.5) | (205.9) |
| Cmin | Mean | — | 3.0 | 6.6 | 14.8 | 26.8 |
| (ng/mL) | (SD) | | (1.0) | (2.1) | (4.3) | (10.1) |
| CL/F | Mean | 39.7 | 26.8 | 24.2 | 26.6 | 21.6 |
| (L/hr) | (SD) | (7.1) | (10.2) | (3.1) | (9.7) | (3.9) |
| CL/F/Wt | Mean | 0.52 | 0.36 | 0.34 | 0.36 | 0.30 |
| (L/hr/kg) | (SD) | (0.08) | (0.14) | (0.05) | (0.14) | (0.07) |
| R | Mean | — | 1.6 | — | — | — |
| | (SD) | | (0.3) | | | |
| $AUC_{0-24}/$ | Mean | — | — | 2.2 | 4.1 | 7.8 |
| $AUC_{0-24}$ 12.5 mg | (SD) | | | (0.4) | (0.8) | (3.4) |

*N indicates the number of subjects in the safety population who took drug. Due to early termination or missing data, some subjects may not be contributing to the results at all time points.

The dose proportionality of the Cmax and $AUC_{0-24}$ of SPD465 d- and l-amphetamine were analyzed using the power model and graphically by plotting individual subject and mean Day 7 Cmax and $AUC_{0-24}$ against dose with the estimated power model regression line. See FIGS. 13-14 and 17-18.

These results showed that repeated doses of SPD465 led to the accumulation of d- and l-amphetamine in plasma consistent with the half-life and dosing of the compound. Further, the Cmax and $AUC_{0-24}$ increased linearly with increasing doses of SPD465. Because SPD465 includes an immediate release bead, a delayed pulsed release bead, and a sustained release bead in a 1:1:1 ratio, the Cmax and $AUC_{0-24}$ for the sustained release bead alone also increases linearly with increasing doses of SPD465 (e.g., the Cmax for 25 mg of the sustained release bead is twice the Cmax for 12.5 mg of the sustained release bead, and the Cmax for 37.5 mg of the sustained release bead is 3× the Cmax for 12.5 mg of the sustained release bead).

The disclosures of patents, patent applications, publications, product descriptions, and protocols cited throughout this application are incorporated by reference in their entireties.

It is to be understood that the scope of the present invention is not to be limited to the specific embodiments described above. The invention may be practiced other than as particularly described and still be within the scope of the accompanying claims.

The invention claimed is:

1. A pharmaceutical composition comprising: (a) an immediate release bead comprising at least one amphetamine salt; (b) a first delayed release bead comprising at least one amphetamine salt; and (c) a second delayed release bead comprising at least one amphetamine salt; wherein the first delayed release bead provides pulsed release of the at least one amphetamine salt and the second delayed release bead provides sustained release of the at least one amphetamine salt;
wherein the second delayed release bead comprises at least one amphetamine salt layered onto or incorporated into a core; a delayed release coating layered onto the amphetamine core; and a sustained release coating layered onto the delayed release coating, wherein the sustained release coating is pH-independent; and
wherein the first delayed release bead and the second delayed release bead comprise an enteric coating.

2. The pharmaceutical composition of claim 1, wherein the enteric coating is pH dependent.

3. The pharmaceutical composition of claim 1, wherein the first delayed release bead and the second delayed release bead comprise different enteric coatings.

4. The pharmaceutical composition of claim 1, wherein the first delayed release bead and the second delayed release bead comprise the same enteric coating.

5. The pharmaceutical composition of claim 1, wherein administration of a 37.5 mg dose of the pharmaceutical composition to a human patient results in a d-amphetamine $C_{max}$ of about 50 ng/ml.

6. The pharmaceutical composition of claim 1, wherein the d-amphetamine area under the curve from time 0 to the last measured time ($AUC_{0-last}$) after administration of a 37.5 mg dose of the pharmaceutical composition to a human patient is about 1058 nghr/ml.

7. The pharmaceutical composition of claim 1, wherein the d-amphetamine area under the curve from time 0 to time infinity ($AUC_{0-inf}$) after administration of a 37.5 mg dose of the pharmaceutical composition to a human patient is about 1085 nghr/ml.

8. The pharmaceutical composition of claim 1, wherein the d-amphetamine $T_{max}$ is about 8.2 hours after administration of a 37.5 mg dose of the pharmaceutical composition to a human patient.

9. The pharmaceutical composition of claim 1, wherein the l-amphetamine $C_{max}$ after administration of a 37.5 mg dose of the pharmaceutical composition to a human patient is about 15 ng/ml.

10. The pharmaceutical composition of claim 1, wherein the l-amphetamine area under the curve from time 0 to the last measured time ($AUC_{0-last}$) after administration of a 37.5 mg dose of the pharmaceutical composition to a human patient is about 354 nghr/ml.

11. The pharmaceutical composition of claim 1, wherein the l-amphetamine area under the curve from time 0 to time infinity ($AUC_{0-inf}$) after administration of a 37.5 mg dose of the pharmaceutical composition to a human patient is about 373 nghr/ml.

12. The pharmaceutical composition of claim 1, wherein the l-amphetamine $T_{max}$ is about 8.4 hours after administration of a 37.5 mg dose of the pharmaceutical composition to a human patient.

13. The pharmaceutical composition of claim 1, wherein the immediate release bead and at least one delayed release bead are present on a single core.

14. The pharmaceutical composition of claim 1, wherein the immediate release bead and at least one delayed release bead are present on different cores.

15. The pharmaceutical composition of claim 1, wherein the at least one amphetamine salt is coated onto a core.

16. The pharmaceutical composition of claim 1, wherein the at least one amphetamine salt is incorporated into a core.

17. The pharmaceutical composition of claim 1, which further comprises a protective layer over at least one enteric coating.

18. The pharmaceutical composition of claim 1, which further comprises a protective layer between the amphetamine salt and at least one enteric coating.

19. The pharmaceutical composition of claim 1, wherein the at least one amphetamine salt is selected from the group consisting of dextroamphetamine sulfate, dextroamphetamine saccharate, amphetamine aspartate monohydrate, amphetamine sulfate, and mixtures thereof.

20. The pharmaceutical composition of claim 19, wherein the at least one amphetamine salt is a mixture of dextroamphetamine sulfate, dextroamphetamine saccharate, amphetamine aspartate monohydrate, and amphetamine sulfate.

21. The pharmaceutical composition of claim 1, wherein the composition does not exhibit a food effect.

22. The composition of claim 1, wherein the amount of at least one amphetamine salt is about 12.5 mg.

23. The composition of claim 1, wherein the amount of at least one amphetamine salt is about 18.75 mg.

24. The composition of claim 1, wherein the amount of at least one amphetamine salt is about 25 mg.

25. The composition of claim 1, wherein the amount of at least one amphetamine salt is about 31.25 mg.

26. The composition of claim 1, wherein the amount of at least one amphetamine salt is about 37.5 mg.

27. The composition of claim 1, wherein the amount of at least one amphetamine salt is about 43.75 mg.

28. The composition of claim 1, wherein the amount of at least one amphetamine salt is about 50 mg.

29. The composition of claim 1, wherein the amount of at least one amphetamine salt is about 62.5 mg.

30. The composition of claim 1, wherein the amount of at least one amphetamine salt is about 75 mg.

31. The pharmaceutical composition of claim 1, wherein a protective coating is layered between the delayed release coating and the sustained release coating.

* * * * *